US008466277B2

(12) United States Patent
Orlando et al.

(10) Patent No.: US 8,466,277 B2
(45) Date of Patent: *Jun. 18, 2013

(54) COUPLING LOW-MOLECULAR SUBSTANCES TO A MODIFIED POLYSACCHARIDE

(75) Inventors: Michele Orlando, The Hague (NL); Jurgen Hemberger, Aschaffenburg (DE); Klaus Sommermeyer, Rosbach (DE); Wolfram Eichner, Butzbach (DE); Sven Frie, Bramois (CH); Katharina Lutterbeck, Friedberg (DE); Cornelius Jungheinrich, Bad Homburg (DE); Roland Scharpf, Ranstadt (DE)

(73) Assignee: Fresenius Kabi Deutschland GmbH, Bad Homburg v.d.H. (DE)

( * ) Notice: Subject to any disclaimer, the term of this patent is extended or adjusted under 35 U.S.C. 154(b) by 797 days.

This patent is subject to a terminal disclaimer.

(21) Appl. No.: 10/506,366

(22) PCT Filed: Feb. 28, 2003

(86) PCT No.: PCT/EP03/02084
§ 371 (c)(1),
(2), (4) Date: Feb. 2, 2005

(87) PCT Pub. No.: WO03/074088
PCT Pub. Date: Sep. 12, 2003

(65) Prior Publication Data
US 2006/0217293 A1    Sep. 28, 2006

(30) Foreign Application Priority Data
Mar. 6, 2002  (DE) .................. 102 09 822

(51) Int. Cl.
| | |
|---|---|
| *C08B 31/00* | (2006.01) |
| *C08B 31/02* | (2006.01) |
| *C08B 31/18* | (2006.01) |
| *C07K 1/00* | (2006.01) |
| *C07K 17/00* | (2006.01) |
| *A61K 31/715* | (2006.01) |
| *C08B 33/00* | (2006.01) |
| *C08B 35/00* | (2006.01) |

(52) U.S. Cl.
USPC .............. 536/45; 536/47; 536/48; 536/102; 536/104; 536/105; 536/106; 536/107; 536/108; 536/109; 536/110; 530/395; 514/60

(58) Field of Classification Search
USPC ........ 536/45, 47, 48, 102, 104–110; 530/395; 514/60
See application file for complete search history.

(56) References Cited

U.S. PATENT DOCUMENTS

| | | | |
|---|---|---|---|
| 3,191,291 A | 6/1965 | Maier | |
| 3,226,395 A | 12/1965 | Schimmelschmidt et al. | |
| 4,001,200 A | 1/1977 | Bonsen et al. | |
| 4,001,401 A | 1/1977 | Bonsen et al. | |
| 4,053,590 A | 10/1977 | Bonsen et al. | |
| 4,061,736 A | 12/1977 | Morris et al. | |
| 4,064,118 A | 12/1977 | Wong | |
| 4,125,492 A | 11/1978 | Cuatrecasas et al. | |
| 4,179,337 A | 12/1979 | Davis et al. | |
| 4,261,973 A | 4/1981 | Lee et al. | |
| 4,412,989 A | 11/1983 | Iwashita et al. | |
| 4,454,161 A | 6/1984 | Okada et al. | |
| 4,496,689 A | 1/1985 | Mitra | |
| 4,667,016 A | 5/1987 | Lai et al. | |
| 4,703,008 A | 10/1987 | Lin | |
| 4,766,106 A | 8/1988 | Katre et al. | |
| 4,847,325 A | 7/1989 | Shadle et al. | |
| 4,863,964 A | 9/1989 | Hedlund et al. | |
| 4,900,780 A | 2/1990 | Cerny | |
| 4,904,584 A | 2/1990 | Shaw | |
| 4,925,677 A | 5/1990 | Feijen | |
| 4,939,239 A | 7/1990 | Matsuhashi et al. | |
| 4,952,496 A | 8/1990 | Studier et al. | |

(Continued)

FOREIGN PATENT DOCUMENTS

| | | |
|---|---|---|
| AU | 5238393 | 9/1993 |
| CA | 2110543 | 2/1993 |

(Continued)

OTHER PUBLICATIONS

Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.

(Continued)

*Primary Examiner* — Wu-Cheng Winston Shen
*Assistant Examiner* — Everett White
(74) *Attorney, Agent, or Firm* — Fish & Richardson P.C.

(57) ABSTRACT

The invention relates to a method for coupling low-molecular weight substances to a starch-derived modified polysaccharide. The binding interaction between the modified polysaccharide and the low-molecular weight substance is based on a covalent bond which is the result of a coupling reaction between the terminal aldehyde group or a functional group of the modified polysaccharide molecule resulting from the chemical reaction of this aldehyde group and a functional group of the low-molecular weight substance which reacts with this aldehyde group or with the resulting functional group of the polysaccharide molecule. The bond directly resulting from the coupling reaction can be optionally modified by a further reaction to the aforementioned covalent bond. The invention further relates to pharmaceutical compositions that comprise conjugates formed in this coupling process and to the use of said conjugates and compositions for the prophylaxis or therapy of the human or animal body.

14 Claims, No Drawings

U.S. PATENT DOCUMENTS

| | | | |
|---|---|---|---|
| 5,068,321 A | 11/1991 | Buysch et al. | |
| 5,073,628 A | 12/1991 | Matsuhashi et al. | |
| 5,079,337 A | 1/1992 | Leonard et al. | |
| 5,110,909 A | 5/1992 | Dellacherie et al. | |
| 5,214,132 A | 5/1993 | Kuga et al. | |
| 5,217,998 A | 6/1993 | Hedlund et al. | |
| 5,218,092 A | 6/1993 | Sasaki et al. | |
| 5,218,108 A * | 6/1993 | Sommermeyer et al. | 536/111 |
| 5,281,698 A | 1/1994 | Nitecki | |
| 5,342,770 A | 8/1994 | Yamasaki | |
| 5,362,853 A | 11/1994 | Kuga et al. | |
| 5,420,105 A | 5/1995 | Gustavson et al. | |
| 5,470,843 A | 11/1995 | Stahl et al. | |
| 5,484,903 A | 1/1996 | Szablikowski et al. | |
| 5,543,332 A | 8/1996 | Lihme et al. | |
| 5,581,476 A | 12/1996 | Osslund | |
| 5,622,718 A | 4/1997 | Al-Shamkhani et al. | |
| 5,723,589 A | 3/1998 | Miljkovic et al. | |
| 5,736,533 A | 4/1998 | Simon et al. | |
| 5,770,645 A | 6/1998 | Stamler et al. | |
| 5,824,778 A | 10/1998 | Ishikawa et al. | |
| 5,840,900 A | 11/1998 | Greenwald et al. | |
| 5,847,110 A | 12/1998 | Dragsten et al. | |
| 5,851,984 A | 12/1998 | Matthews et al. | |
| 5,876,980 A | 3/1999 | DeFrees et al. | |
| 5,880,270 A | 3/1999 | Berninger et al. | |
| 5,952,347 A | 9/1999 | Arison et al. | |
| 5,977,163 A | 11/1999 | Li et al. | |
| 5,981,507 A | 11/1999 | Josephson et al. | |
| 5,990,237 A | 11/1999 | Bentley et al. | |
| 6,011,008 A * | 1/2000 | Domb et al. | 514/8 |
| 6,083,909 A | 7/2000 | Sommermeyer et al. | |
| 6,172,208 B1 | 1/2001 | Cook | |
| 6,261,800 B1 | 7/2001 | Nikolics et al. | |
| 6,299,881 B1 | 10/2001 | Lees et al. | |
| 6,340,746 B1 | 1/2002 | Roberts et al. | |
| 6,375,846 B1 | 4/2002 | Jarrett et al. | |
| 6,395,266 B1 | 5/2002 | Martinez et al. | |
| 6,417,347 B1 | 7/2002 | Herrmann et al. | |
| 6,451,337 B1 | 9/2002 | Smith et al. | |
| 6,500,930 B2 | 12/2002 | Adamson | |
| 6,544,503 B1 | 4/2003 | Vanderhoff et al. | |
| 6,555,660 B2 | 4/2003 | Nissen et al. | |
| 6,586,398 B1 | 7/2003 | Kinstler et al. | |
| 6,596,135 B2 | 7/2003 | Mitsui | |
| 6,596,861 B1 | 7/2003 | Moreau | |
| 6,624,142 B2 | 9/2003 | Greenwald et al. | |
| 6,660,843 B1 | 12/2003 | Feige et al. | |
| 6,875,594 B2 | 4/2005 | Muir | |
| 6,916,962 B2 | 7/2005 | Rosen et al. | |
| 7,115,576 B2 | 10/2006 | Sommermeyer | |
| 7,125,843 B2 | 10/2006 | DeFrees et al. | |
| 7,157,546 B2 | 1/2007 | Kozlowski | |
| 7,179,617 B2 | 2/2007 | DeFrees et al. | |
| 7,279,176 B1 | 10/2007 | West et al. | |
| 7,285,661 B2 * | 10/2007 | Sommermeyer et al. | 536/45 |
| 7,538,092 B2 | 5/2009 | Orlando et al. | |
| 7,541,328 B2 * | 6/2009 | Hemberger et al. | 514/2 |
| 7,629,456 B2 | 12/2009 | Lange et al. | |
| 7,815,893 B2 | 10/2010 | Zander et al. | |
| 8,017,739 B2 | 9/2011 | Eichner et al. | |
| 2002/0065410 A1 | 5/2002 | Antrim | |
| 2003/0087877 A1 | 5/2003 | Calias et al. | |
| 2003/0191291 A1 | 10/2003 | Kochendoerfer et al. | |
| 2004/0023306 A1 | 2/2004 | Aebersold et al. | |
| 2004/0043446 A1 | 3/2004 | DeFrees et al. | |
| 2004/0180858 A1 | 9/2004 | Sommermeyer | |
| 2005/0063943 A1 | 3/2005 | Sommermeyer et al. | |
| 2005/0181985 A1 | 8/2005 | Hemberger et al. | |
| 2005/0238723 A1 | 10/2005 | Zander et al. | |
| 2006/0019877 A1 | 1/2006 | Conradt et al. | |
| 2006/0121062 A1 | 6/2006 | Eichner et al. | |
| 2006/0188472 A1 | 8/2006 | Sommermeyer et al. | |
| 2006/0194940 A1 | 8/2006 | Kozlowski | |
| 2006/0217293 A1 | 9/2006 | Orlando et al. | |
| 2007/0087961 A1 | 4/2007 | Eichner et al. | |
| 2007/0134197 A1 | 6/2007 | Eichner et al. | |
| 2008/0206182 A1 | 8/2008 | Sommermeyer et al. | |
| 2008/0207562 A1 | 8/2008 | Zander et al. | |
| 2008/0274948 A1 | 11/2008 | Eichner et al. | |
| 2009/0091549 A1 | 4/2009 | Matsumoto et al. | |
| 2009/0233847 A1 | 9/2009 | Hemberger et al. | |
| 2010/0062973 A1 | 3/2010 | Frank et al. | |
| 2010/0297078 A1 | 11/2010 | Hacket et al. | |
| 2010/0305033 A1 | 12/2010 | Hacket et al. | |
| 2010/0311670 A1 | 12/2010 | Zander et al. | |
| 2010/0317609 A1 | 12/2010 | Zander et al. | |
| 2011/0054152 A1 | 3/2011 | Zander et al. | |
| 2011/0200555 A1 | 8/2011 | Eichner et al. | |
| 2012/0046240 A9 | 2/2012 | Zander et al. | |

FOREIGN PATENT DOCUMENTS

| | | |
|---|---|---|
| CA | 2 233 725 | 9/1999 |
| CA | 2 441 442 | 9/2003 |
| CA | 2 478 478 | 1/2004 |
| CA | 2 478 480 | 1/2004 |
| DE | 22 33 977 | 2/1973 |
| DE | 2607706 | 9/1976 |
| DE | 26 46 854 | 5/1977 |
| DE | 26 16 086 | 11/1977 |
| DE | 30 29 307 | 3/1982 |
| DE | 30 29 307 | 4/1982 |
| DE | 3501616 | 7/1986 |
| DE | 38 36 600 | 5/1990 |
| DE | 279 486 | 6/1990 |
| DE | 41 30 807 | 3/1993 |
| DE | 69025920 | 8/1996 |
| DE | 196 28 705 | 1/1998 |
| DE | 198 08 079 | 8/1999 |
| DE | 101 12 825 | 2/2002 |
| DE | 100 41 541 | 3/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 138 572 | 4/1985 |
| EP | 0 218 825 | 4/1987 |
| EP | 0 243 929 | 11/1987 |
| EP | 0 304 183 | 2/1989 |
| EP | 0 307 827 | 3/1989 |
| EP | 0 315 349 | 5/1989 |
| EP | 331471 A * | 9/1989 |
| EP | 0 338 916 | 10/1989 |
| EP | 0 402 724 | 6/1990 |
| EP | 0 148 605 | 7/1990 |
| EP | 0 205 564 | 5/1991 |
| EP | 0 428 267 | 5/1991 |
| EP | 0 411 678 | 1/1992 |
| EP | 0 127 839 | 7/1992 |
| EP | 0 331 471 | 12/1992 |
| EP | 0 549 721 | 4/1994 |
| EP | 0 605 963 | 7/1994 |
| EP | 0 609 968 | 8/1994 |
| EP | 0 342 557 | 11/1994 |
| EP | 0 661 294 | 12/1994 |
| EP | 0 640 619 | 3/1995 |
| EP | 0 646 130 | 4/1995 |
| EP | 0 418 523 | 6/1995 |
| EP | 0 668 351 | 8/1995 |
| EP | 0 809 996 | 5/1996 |
| EP | 0 806 140 | 11/1997 |
| EP | 1 230 935 | 8/2002 |
| EP | 1 400 533 | 9/2002 |
| EP | 1 398 322 | 9/2003 |
| EP | 1 398 327 | 9/2003 |
| EP | 1 398 328 | 9/2003 |
| EP | 1 424 086 | 6/2004 |
| EP | 1496076 | 1/2005 |
| EP | 1591467 | 11/2005 |
| EP | 1 064 951 | 8/2007 |
| EP | 2 070 950 | 6/2009 |
| EP | 2 143 736 | 1/2010 |

| | | |
|---|---|---|
| EP | 2 154 160 | 2/2010 |
| EP | 1660134 | 12/2010 |
| EP | 1372735 | 10/2011 |
| FR | 2 378 094 | 8/1978 |
| GB | 1 419 080 | 12/1975 |
| GB | 1 549 246 | 10/1976 |
| GB | 1 540 428 | 2/1979 |
| IL | 166506 | 2/2010 |
| JP | 10-287554 | 10/1998 |
| JP | 2001-294601 | 10/2001 |
| WO | WO 80/02374 | 11/1980 |
| WO | WO 90/07939 | 7/1990 |
| WO | 90/12874 | 11/1990 |
| WO | WO 90/15628 | 12/1990 |
| WO | WO 92/11037 | 7/1992 |
| WO | WO 93/23062 | 11/1993 |
| WO | 93/24476 | 12/1993 |
| WO | WO 94/01483 | 1/1994 |
| WO | WO 94/05332 | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |
| WO | WO 97/38727 | 10/1997 |
| WO | WO 97/42225 | 11/1997 |
| WO | WO 98/01158 | 1/1998 |
| WO | 98/07713 | 2/1998 |
| WO | WO 98/05689 | 2/1998 |
| WO | WO 98/08856 | 3/1998 |
| WO | 98/14212 | 4/1998 |
| WO | WO 98/14215 | 4/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | WO 99/17783 | 4/1999 |
| WO | 99/49897 | 10/1999 |
| WO | WO 99/49897 | 10/1999 |
| WO | 00/07738 | 2/2000 |
| WO | WO 00/18893 | 4/2000 |
| WO | WO 00055210 | 9/2000 |
| WO | WO 00/66633 | 11/2000 |
| WO | WO 00/78355 | 12/2000 |
| WO | WO 01/70272 | 9/2001 |
| WO | 01/78682 | 10/2001 |
| WO | WO 01/83522 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/80979 | 10/2002 |
| WO | WO 03/000738 | 1/2003 |
| WO | WO 03/031464 | 4/2003 |
| WO | WO 03/031581 | 4/2003 |
| WO | WO 03/035665 | 5/2003 |
| WO | WO 03/049699 | 6/2003 |
| WO | WO 03/059246 | 7/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | WO 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | 2005/072778 | 8/2005 |
| WO | WO 2005/074993 | 8/2005 |
| WO | WO 2005/083103 | 9/2005 |
| WO | 2005/092369 | 10/2005 |
| WO | WO 2005/092390 | 10/2005 |
| WO | 2005/112954 | 12/2005 |
| WO | WO 2006/108052 | 10/2006 |
| WO | WO 2007/053292 | 5/2007 |
| WO | WO 2010/042638 | 4/2010 |

OTHER PUBLICATIONS

Alayash and Cashon, "Hemoglobin and free radicals: implications for the development of a safe blood substitute," *Molec. Med. Today*, 1995, 1(3):122-127.

Ashwell, "Carbohydrate Antigens: Coupling of Carbohydrates to Proteins by a Mixed Anhydride Reaction," *Meth. Enzymol.*, 1972, 28:219-222.

Avigad, "A Simple Spectrophotometric Determination of Formaldehyde and Other Aldehydes: Application to Periodate-Oxidized Glycol Systems," *Anal. Biochem.*, 1983, 134:499-504.

Baldwin et al., "Synthesis of Polymer-Bound Hemoglobin Samples," *Tetrahedron*, 1981, 37:1723-1726.

Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.

Barbone et al., "Reticulocyte measurements as a bioassay for erythropoietin," *J. Pharm. Biomed. Anal.*, 1994, 12(4):515-522.

Bårström et al., "New derivatives of reducing oligosaccharides and their use in enzymatic reactions: efficient synthesis of sialyl Lewis a and sialyl dimeric Lewis x glycoconjugates," *Carbohydr. Res.*, 2000, 328:525-531.

Bauer et al., "Synthesis of w—(Aminooxy)alkanethiols," *J. Org. Chem.*, 1965, 30:949-951.

Bauer and Suresh, "S-[w-(Aminoöxy)alkyl]isothiuronim Salts, w,w'-Bis(aminoöxy)alkanes and Related Compounds," *J. Org. Chem.*, 28:1604-1608.

Bendele et al., "Short Communication: Renal Tubular Vacuolation in Animals Treated with Polyethylene-Glycol-Conjugated Proteins," *Toxicol. Sci.*, 1998, 42:152-157.

Benesch, "Bis(pyridoxal) Polyphosphates as Specific Intramolecular Cross-Linking Agents for Hemoglobin," *Meth. Enzymol.*, 1994, 231:267-274.

Bepperling et al., "HES 130/0.4, a new HES specification: tissue storage after multiple infusions in rats," *Crit. Care*, 1999, 3(suppl 1):P153.

Berger et al., "Galactosyltransferase-dependent sialylation of complex and endo-N-acetylglucosaminidase H-treated core N-glycans in vitro," *FEBS Lett.*, 1986, 203(1):64-68.

Black et al., "N-Bromoacetyl-glycopyranosylamines as affinity labels for a β-glucosidase and a cellulase," *Carbohydr. Res.*, 1993, 250:195-202.

Bobbitt, "Periodate Oxidation of Carbohydrates," *Carbohydr. Chem.*, 1956, 11:1-41.

Boissel et al., "Erythropoietin Structure-Function Relationships. Mutant proteins that test a model of tertiary structure," *J. Biol. Chem.*, 1993, 268(21):15983-15993.

Boturyn et al., "Synthesis of Fluorescent Probes for the Detection of Abasic Sites in DNA," *Tetrahedron*, 1997, 53(15):5485-5492.

Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.

Bronzino, *The Biomedical Engineering Handbook*, CRC Press, USA, Salem, 1995, (TOC only).

Bunn & Jandl, "The Renal Handling of Hemoglobin. II. Catabolism," *J. Exp. Med.*, 1967, 129:925-934.

Burgess et al., "Stimulation by Human Placental Conditioned Medium of Hemopoietic Colony Formation by Human Marrow Cells," *Blood*, 1977, 49(4):573-583.

Bystrický et al., "Determination of the cross-linking effect of adipic acid dihydrazide on glycoconjugate preparation,"*Glycoconj. J.*, 1999, 16:691-695.

Cabacungan et al., "Amine Boranes as Alternative Reducing Agents for Reductive Alkylation of Proteins," *Anal. Biochem.*, 1982, 124:272-278.

Carlsson et al., "Protein Thiolation and Reversible Protein-Protein Conjugation," *Biochem J.*, 1978, 173:723-737.

Cerami, "Beyond Erythropoiesis: Novel Applications for Recombinant Human Erythropoietin," *Semin. Hematol.*, 2001, 38:(3 Suppl 7):33-39.

Cerny et al., "A Hydroxyethyl Starch-Hemoglobin Polymer as a Blood Substitute," *Clinical Hemorheology*, 1982, 2(4):355-365.

Chamow et al., "Conjugation of Soluble CD4 without Loss of Biological Activity via a Novel Carbohydrate-directed Cross-linking Reagent," *J. Biol. Chem.*, 1992, 267(22):15916-15922.

Chang, "Blood Substitutes Based on Modified Hemoglobin Prepared by Encapsulation or Crosslinking: An Overview," *Biomat., Art. Cells & Immob. Biotech.*, 1992, 20:159-179.

Chagnon et al., "Murine renal cell carcinoma: evaluation of a dendritic-cell tumour vaccine," *BJU Int.*, 2001, 88:418-424.

Chaplin, "Monosaccharides," *Carbohydrate analysis: a practical approach*, 1996, Chaplin and Kennedy (eds.), Chapter 1, "Oligosacchardies," pp. 37-54.

Chaplin, "A Rapid and Sensitive Method for the Analysis of Carbohydrate Components in Glycoproteins Using Gas-Liquid Chromatography," *Anal. Biochem.*, 1982, 123:336-341.

Chapman et al., "Therapeutic antibody fragments with prolonged in vivo half-lives," *Nature Biotech.*, 1999, 17:780-783.

Chow et al., "In vitro Induction of apoptosis of neoplastic cells in low-grade non-Hodgkin's lymphomas using combinations of established cytotoxic drugs with bendamustine," *Haematologica*, 2001, 86:485-493.

Chu et al., "Further Studies on the Immunogenicity of *Haemophilus influenzae* Type b and Pneumococcal Type 6A Polysaccharide-Protein Conjugates," *Infect. Immun.*, 1983, 40:245-256.

Cumber et al., "Preparation of Antibody-Toxin Conjugates," *Meth. Enzymol.*, 1985, 112:207-225.

Delgado et al., "The Uses and Properties of PEG-Linked Proteins," *Crit. Rev. Ther. Drug Carrier Syst.*, 1992, 9(3,4):249-304.

Delorme et al., "Role of Glycosylation on the Secretion and Biological Activity of Erythropoietin," *Biochemistry*, 1992, 31(41):9871-9876.

Dittmar et al., "Human Glycoproteins and Derived Variants from Recombinant Mammalian Cell Lines," *Advances in Protein Design*, 1989, 12:145-156.

Dowling and Russell, "Pharmacokinetics of a long-acting oxytetracycline-polyethylene glycol formulation in horses," *J. Vet. Pharmacol. Therap.*, 2000, 23:107-110.

Dreborg and Åkerblom, "Immunotherapy with Monomethoxypolyethylene Glycol Modified Allergens," *Crit. Rev. Ther. Drug Carrier Syst.*, 1990, 6(4):315-365.

Edmunds et al., "Transgenically Produced Human Antithrombin: Structural and Functional Comparison to Human Plasma-Derived Antithrombin," *Blood*, 1998, 91(12):4561-4571.

Blum et al., "Improved silver staining of plant proteins, RNA and DNA in polyacrylamide gels," *Electrophoresis*, 1987, 8:93-99.

Elliott et al., "Mapping of the Active Site of Recombinant Human Erythropoietin," *Blood*, 1997, 89(2): 493-502.

European Pharmacopoeia, "Erythropoietin Concentrated Solution," 3rd Edition, 2000, Monography, pp. 655-660.

European Pharmacopoeia, "Erythropoietin Concentrated Solution," 4th Edition, 2002, Monography, pp. 1123-1128.

Fernández-Santana et al., "Conjugation of 5-azido-3-oxapentyl glycosides with thiolated proteins through the use of thiophilic derivatives," *Glycoconj. J.*, 1998, 15:549-553.

Fibi et al., "Evidence for the Location of the Receptor-Binding Site of Human Erythropoietin at the Carboxyl-Terminal Domain," *Blood*, 1991, 77(6):1203-1210.

Fibi et al., "N- and O-Glycosylation Muteins of Recombinant Human Erythropoietin Secreted From BHK-21 Cells," *Blood*, 1995, 85(5):1229-1236.

Fissekis et al., "*N*-Pantyol-(substituted)amines, Pantothenic Acid Analogues," *J. Med. Pharm. Chem.*, 1960, 2:47-56.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271:907-919.

Gaertner and Offord, "Site-Specific Attachment of Functionalized Poly(ethylene glycol) to the Amino Terminus of Proteins,"*Biocodugate Chemistry*, 1996, 7(1):38-44.

Gervais et al., "NMR investigations of the role of the sugar moiety in glycosylated recombinant human granulocyte-colony-stimulating factor," *Eur. J. Biochem.*, 1997, 247:386-395.

Gillis et al., "T Cell Growth Factor: Parameters of Production and a Quantitative Microassay for Activity," *J. Immunol.*, 1978, 120(6):2027-2032.

Gonzalez Lio and Thiem, "Chemoenzymatic synthesis of spacer-linked oligosaccharides for the preparation of neoglycoproteins," *Carbohydr. Res.*, 1999, 317:180-190.

Gould et al., "The Development of Hemoglobin Solutions as Red Cell Substitutes: Hemoglobin Solutions," *Transfus. Sci.*, 1995, 16:5-17.

Grabenhorst et al., "Construction of stable BHK-21 cells coexpressing human secretory glycoproteins and human Gal($\alpha$1-4)GlcNAc-R $\alpha$2,6-sialyltransferase: $\beta$2,6-Linked NeuAc is preferentially attached to the Gal($\beta$1-4)GlcNAc($\beta$1-2)Man($\alpha$1-3)-branch of diantennary oligosaccharides from secreted recombinant $\beta$-trace protein," *Eur. J. Biochem.*, 1995, 232:718-725.

Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.

Grabenhorst et al., "In Vivo Specificity of Human $\alpha$1,3/4-Fucosyltransferases III-VII in the Biosynthesis of Lewis$^x$ and Sialyl Lewis$^x$ Motifs on Complex-type *N*-Glycans. Coexpression studies from BHK-21 cells together with human $\beta$-trace protein," *J. Biol. Chem.*, 1998, 273(47):30985-30994.

Grabenhorst et al., "Genetic engineering of recombinant glycoproteins and the glycosylation pathway in mammalian host cells," *Glycoconj J.*, 1999, 16(2):81-97.

Gray, "The Direct Coupling of Oligosaccharides to Proteins and Derivatized Gels,"*Arch. Biochem. Biophys.*, 1974, 163:426-428 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Grimmecke and Brade, "Studies on the reductive amination of 3-deoxy-D-*manno*-octulosonic acid (Kdo)," *Glycoconj. J.*, 1998, 15:555-562.

Habeeb, "Determination of Free Amino Groups in Proteins by Trinitrobenzenesulfonic Acid," Anal. Biochem., 1966, 14:328-336.

Hai et al., "Diaspirin Crosslinked Hemoglobin (DCLHb™) Polymerization," *Art. Cells, Blood Subs., and Immob. Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylation of Its Hydroxyl Groups," *J. Polymer Science: Part A: Polymer Chemistry*, 1991, 29:1271-1279.

Hattori et al., "Reduced Immunogenicity of β-Lactoglobulin by Conjugation with Carboxymethyl Dextran," *Bioconjug. Chem.*, 2000, 11:84-93.

Herman et al., "Characterization, Formulation, and Stability of Neupogen® (Filgrastim), a Recombinant Human Granulocyte-Colony Stimulating Factor," *Formulation Characterization, and Stability of Protein Drugs*, Pearlman and Wang (eds.), Plenum Press, Chapter 7, 1996, pp. 303-328.

Hermanson, *Bioconjugate Techniques*, 1996 (TOC only).

Hermentin et al., "A Strategy for the Mapping of N-Glycans by High-pH Anion-Exchange Chromatography with Pulsed Amperometric Detection," *Anal. Biochem.*, 1992, 203(2):281-289.

Higuchi et al., "Role of Sugar Chains in the Expression of the Biological Activity of Human Erythropoietin," *J. Biol. Chem.*, 1992, 267(11):7703-7709.

Sharaf et al., "Studies on Aroyl- and Aryl-Hydrazide Derivatives from D-*glycero*-D-*gulo*-Heptono-1,4-Lactone," *Carbohydrate Res.*, 1981, 91:39-48.

Inoue et al., "An Improved Method for the Purification of Human Erythropoietin with High in Vivo Activity from the Urine of Anemic Patients," *Biol. Pharm. Bull.*, 1994, 17(2):180-184.

Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.

Jia et al., "S-nitrosohaemoglobin: a dynamic activity of blood involved in vascular control," *Nature*, 1996, 380:221-226.

Jones et al., "A convenient synthesis of N-(tert-butyloxycarbonyl)aminooxy ethers," *Tetrahedron Letters*, 2000, 41(10):1531-1533.

Jones et al., "Multivalent Poly(ethylene glycol)-Containing Conjugates for In Vivo Antibody Suppression," *Bioconj. Chem.*, 2003, 14(6):1067-1076.

Kallin, "Coupling of Oligosaccharides to Proteins Using *p*-Trifluoroacetamidoaniline," *Meth. Enzymol.*, 1994, 242:119-123.

Keaney, Jr. et al., "NO Forms an Adduct with Serum Albumin that Has Endothelium-derived Relaxing Factor-like Properties," *J. Clin. Invest.*, 1993, 91:1582-1589.

Keipert et al., "Functional properties of a new crosslinked hemoglobin designed for use as a red cell substitute," *Transfusion*, 1989, 29:768-773.

Kitamura et al., "Establishment and Characterization of a Unique Human Cell Line That Proliferates Dependently on GM-CSF, IL-3, or Erythropoietin," *J. Cell. Phys.*, 1989, 140:323-334.

Kitamura et al., "Chemical Engineering of the Monoclonal Antibody A7 by Polyethylene Glycol for Targeting Cancer Chemotherapy," *Cancer Res.*, 1991, 51:4310-4315.

Kleine-Tebbe et al., "Allergen Immunotherapy—A Position Paper of the German Society for Allergology and Clinical Immunology," *Pneumologie*, 2001, 55:438-444.

Klemm et al., "Esterification of Cellulose," *Comprehensive Cellulose Chemistry*, 1998, vol. 2, Wiley-VCH, Weinheim, New York, especially chapter 4.4, pp. 99-207.

Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.

Kojima et al., "Mitomycin C-dextran conjugate: a novel high molecular weight pro-drug of mitomycin C," *J. Pharm. Pharmacol.*, 1980, 32:30-34.

Komatsu et al., "Cloning of granulocyte colony-stimulating factor cDNA from human macrophages and its expression in *Escherichia coli*," *Jpn. J. Cancer Res.*, 1987, 78(11):1179-1181.

Krantz, "Erythropoietin," *Blood*, 1991, 77(3):419-434.

Krystal, "Physical and Biological Characterization of Erythroblast Enhancing Factor (EEF), a Late Acting Erythropoietic Stimulator in Serum Distinct from Erythropoietin," *Exp. Hematol.*, 1983, 11(1):18-31.

Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.

Krystal et al., "Purification of Human Erythropoietin to Homogeneity by a Rapid Five-Step Procedure," *Blood*, 1986, 67(1):71-79.

Kuberan et al., "Preparation and isolation of neoglycoconjugates using biotin-streptavidin complexes," *Glycoconj. J.*, 1999, 16:271-281.

Kurtz and Eckardt, "Assays for Erythropoietin," *Nephron.*, 1989, 51(suppl 1):11-14.

Larionova et al., "Conjugation of the Bowman-Birk Soybean Proteinase Inhibitor with Hydroxyethylstarch," *Appl. Biochem. Biotech.*, 1997, 62:175-182.

Lee (ed.), "Synthesis of Peptides and Proteins," *Peptide and Protein Drug Delivery*, 1991, p. 65.

Lee and Lee, "Neoglycoproteins," *Glycoproteins II*, 1997, Chapter 17, Elsevier Science B.V., pp. 301-620.

Leenders et al., "β-Glucuronyl Carbamate Based Pro-moieties Designed for Prodrugs in ADEPT," *Tetrahedron Letters*, 1995, 36(10):1701-1704.

Lee et al., "Activation of soluble polysaccharides with 1-cyano-4-dimethylaminopyridinium tetrafluoroborate for use in protein-polysaccharide conjugate vaccines and immunological reagents," *Vaccine*, 1996, 14(3):190-198.

Lesnefsky et al., "High-Dose Iron-Chelator Therapy During Reperfusion with Deferoxamine-Hydroxyethyl Starch Conjugate Fails to Reduce Canine Infarct Size," *J. Cardiovasc. Pharmacol.*, 1990, 16(4):523-528.

Levy et al., "Recombinant Antithrombin: Production and Role in Cardiovascular Disorder," *Sem. Thromb. Hem.*, 2001, 27(4):405-416.

Lin et al., "Cloning and expression of the human erythropoietin gene," *Proc. Natl. Acad. Sci. USA*, 1985, 82:7580-7584.

Lindsey at al., "Porphyrin Building Blocks for Modular Construction of Bioorganic Model Systems," *Tertrahedron*, 1994, 50(30):8941-8968, especially p. 8956.

Lomant and Fairbanks, "Chemical Probes of Extended Biological Structures: Synthesis and Properties of the Cleavable Protein Crosslinking Reagent [$^{35}$S]Dithiobis(succinimidyl propionate)," *J. Mol. Biol.*, 1976, 104:243-261.

Lönngren and Goldstein, "Coupling of Aldobionic Acids to Proteins Using Water-Solube Carbodiimide," *Meth. Enzymol.*, 1994, 242:116-118.

Manger et al., "1-N-Glycyl β-Oligosaccharide Derivatives as Stable Intermediates for the Formation of Glycoconjugate Probes," *Biochemistry*, 1992, 31:10724-10732.

Manger et al., "Synthesis of 1-N-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.

Maout et al., "Hydroxyethylstarch Conjugated to Human Hemoglobin for use in Blood Tranfusion: Comparison with Dextran Conjugates," *Carbohydrates and Carbohydrate Polymers—Analysis, Biotechnology, Modification, Antiviral and Other Applications*, 1993, Chapter 12, pp. 132-140.

McMahon et al., "Pharmacokinetics and Effects of Recombinant Human Erythropoietin After Intravenous and Subcutaneous Injections in Healthy Volunteers," *Blood*, 1990, 76(9):1718-1722.

Meinjohanns et al., "Novel sequential solid-phase synthesis on N-linked glycopeptides from natural sources," *J. Chem. Soc., Perkin Trans. 1*, 1998, 1:549-560.

Mikola and Hänninen, "Introduction of Aliphatic Amino and Hydroxy Groups to Keto Steroids Using O-Substituted Hydroxylamines," *Bioconj. Chem.*, 1992, 3(2):182-186.

Minnema et al., "Recombinant human antithrombin III improves survival and attenuates inflammatory responses in baboons lethally challenged with *Escherichia coli*," *Blood*, 2000, 95:(4): 1117-1123.

Miyake et al., "Purification of Human Erythropoietin," *J. Biol. Chem.*, 1977, 252(15):5558-5564.

Montreuil et al., "Hexuronic acids," *Carbohydrate analysis: a practical approach*, 1996, Chaplin and Kennedy (eds.), Chapter 5, pp. 175-204.

Mosbech et al., "Hyposensitization in asthmatics with mPEG-modified and unmodified house dust mite extract," *Allergy*, 1990, 45(2):130-141.

Mosmann, "Rapid Colorimetric Assay for Cellular Growth and Survival: Application to Proliferation and Cytotoxicity Assays," *J. Immunol. Meth.*, 1983, 65:55-63.

Mueller et al., "Recombinant Glycoprotein Product Quality in Proliferation-Controlled BHK-21 Cells," *Biotechnol. Bioeng.*, 1999, 65(5):529-536.

Davis and Flitsch, "A Novel Method for the Specific Glycosylation of Proteins," *Tetrahedron Lett.*, 1991, 32(46):6793-6796.

Nagata et al., "The chromosomal gene structure and two mRNAs for human granulocyte colony-stimulating factor," *EMBO J.*, 1986, 5(3):575-581.

Nagata et al., "Molecular cloning and expression of cDNA for human granulocyte colony-stimulating factor," *Nature*, 1986, 319:415-418.

Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.

Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.

Nimtz et al., "Structural characterization of the oligosaccharide chains of native and crystallized boar seminal plasma spermadhesin PSP-I and PSP-II glycoforms," *Eur. J. Biochem.*, 1999, 265:703-718.

Nimtz et al., "Structures of sialylated oligosaccharides of human erythropoietin expressed in recombinant BHK-21 cells," *Eur. J. Biochem.*, 1993, 213:39-56.

Nimtz et al., "Carbohydrate structures of a human tissue plasminogen activator variant expressed in recombinant Chinese hamster ovary cells," *FEBS Lett.*, 1990, 271:14-18.

Nohynek et al., "Comparison of the potency of glycosylated and nonglycosylated human granulocyte colony-stimulating factors in neutropenic and nonneutropenic CD rats," *Cancer Chemother Pharmacol.*, 1997, 39:259-266.

Nomura et al., "Pharmacokinetic characteristics and therapeutic effects of mitomycin C-dextran conjugates after intratumoural injection," *J. Controlled Release*, 1998, 52:239-252.

O'Shannessy and Wilchek, "Immobilization of Glycoconjugates by Their Oligosaccharides: Use of Hydrazido-Derivatized Matrices," *Analytical Biochemistry*, 1990, 191:1.

Pawlowski et al., "A new method of non-cross-linking conjugates of polysaccharides to protein via thioether bonds for the preparation of saccharide-protein conjugate vaccines," *Vaccine*, 1999, 17:1474-1483.

Pazur, "Neutral polysaccharides," *Carbohydrate analysis: a practical approach*, 1996, Chaplin and Kennedy (eds.), Chapter 3, pp. 55-96.

Pedley et al., "The potential for enhanced tumour localization by poly)ethylene glycol) modification of anti-CEA antibody," *Br. J. Cancer.*, 1994, 70:1126-1130.

Peeters et al., "Comparison of four bifunctional reagents for coupling peptides to proteins and the effect of the three moieties on the immunogenicity of the conjugates," *J. Immunol. Meth.*, 1989, 120:133-143.

Peron et al., "Hydroxyethyl starch-induced renal insufficiency after plasma exchange in a patient with polymyositis and liver cirrhosis," *Clin. Nephrol.*, 2001, 55(5):408-411.

*Pharma Business*, Jul./Aug. 2000, pp. 45-60.

Quelle et al., "High-Level Expression and Purification of a Recombinant Human Erythropoietin Produced Using a Baculovirus Vector," *Blood*, 1989, 74(2):652-657.

Rabiner et al., "Evaluation of a stroma-free hemoglobin solution for use as a plasma expander," *J. Exp. Med.*, 1967, 126:1127-1142.

Ragupathi et al., "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm," *Glycoconj. J.*, 1998, 15:217-221.

Ramos et al., "Enzymatic Synthesis of Neoglycopeptide Building Blocks," *Angew. Chem. Int. Ed.*, 2000, 39(2):396-398.

Reidhaar-Olson et al., "Identification of Residues Critical to the Activity of Human Granulocyte Colony-Stimulating Factor," *Biochemistry*, 1996, 35:9034-9041.

Relihan et al., "Clearance Rate and Effect on Renal Function of Stroma-Free Hemoglobin Following Renal Ischemia," *Ann. Surg.*, 1972, 176(6):700-704.

Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.

Rogers et al., "Effects of polymerization on the oxygen carrying and redox properties of diaspirin cross-linked hemoglobin," *Biochim. Biophys. Acta*, 1995, 1248:135-142.

Rohrling et al., "Synthesis and testing of a novel fluorescene label for carbonyls in carbohydrates and cellulosics," *Synlett*, 2001, 5:682-684.

Rose, "Facile Synthesis of Homogeneous Artificial Proteins," *J. Am. Chem. Soc.*, 1994, 116:30-33.

Rudolph et al., "Circulation persistence and biodistribution of lyophilized liposome-encapsulated hemoglobin: An oxygen-carrying resuscitative fluid," *Crit. Care Med.*, 1994, 22:142-150.

Rudolph, "The Freeze-Dried Preservation of Liposome Encapsulated Hemoglobin: A Potential Blood Substitute," *Cryobiology*, 1988, 25:277-284.

Rush et al., "Microheterogeneity of Erythropoietin Carbohydrate Structure," *Anal. Chem.*, 1995, 67(8):1442-1452.

Ruttmann et al., "In vivo investigation into the effects of haemodilution with hydroxyethylstarch (200/0.5) and normal saline on coagulation," *Br. J. Anaesthesia*, 1998, 80(5):612-616.

Sadamoto et al., "Control of Bacteria Adhesion by Cell-Wall Engineering," *J. Am. Chem. Soc.*, 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.

Sakai et al., "Synthesis and Physicochemical Characterization of a Series of Hemoglobin-Based Oxygen Carriers: Objective Comparison between Cellular and Acellular Types," *Bioconj. Chem.*, 2000, 11:56-64.

Sato et al., "Disposition of a Polymeric Prodrug of Mitomycin C, Mitomycin C-Dextran Conjugate, in the Perfused Rat Liver," *J. Pharm. Sci.*, 1989, 78:11-16.

Sawaikar et al., "Products active on mosquitoes. Part VII, Synthesis and biological activity of longifolene derivatives," *Indian Journal of Chemistry*, 1995, 34B:832-835.

Scaglione et al., "A New Model Examining Intracellular and Extracellular Activity of Amoxicillin, Azithromycin, and Clarithromycin in Infected Cells," *Chemotherapie*, 1993, 39:416-423.

Schäfer et al., "Two-year double-blind trial of a monomethoxy polyethylene glycol (mPEG) modified grass pollen extract at different dose levels," *Ann. Allergy*, 1992, 68(4):334-339.

Schlenke et al., "Construction and characterization of stably transfected BHK-21 cells with human-type sialylation characteristic," *Cytotechnology*, 1999, 30:17-25.

Schottelius et al., "Improvement of Pharmacokinetics of Radioiodinated Tyr[3]-Octreotide by Conjugation with Carbohydrates," *Bioconjugate Chem.*, 2002, 13:1021-1030.

Schröter et al., "Male-specific Modification of Human CD52," *J. Biol. Chem.*, 1999, 274(42):29862-29873.

Shafer et al., "Activation of soluble polysaccharides with 1-cyano-4-dimethylaminopyridinium tetrafluoroborate (CDAP) for use in protein-polysaccharide conjugate vaccines and immunolgical reagents. II. Selective crosslinking of proteins to CDAP-activated polysaccharides," *Vaccine*, 2000, 18:1273-1281.

Shah et al., "Characterization of Colony-stimulating Activity Produced by Human Monocytes and Phytohemagglutinin-stimulated Lymphocytes," 1977, *Blood*, 50(5):811-821.

Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.

Simmons et al., "Potent inhibition of HIV-1 infectivity in macrophages and lymphocytes by a novel CCR5 antagonist," *Science*, 1997, 276:276-279.

Snyder et al., "HbXL99α: A hemoglobin derivative that is cross-linked between the α subunits is useful as a blood substitute," *Proc. Natl. Acad. Sci. USA*, 1987, 84:7280-7284.

Shu, "Somogyi Micro Copper Method," *Method in Carbohydride Chemistry*, 1962, 1:383-388.
Song et al., "Toxicity and Antitumor Activity of the Conjugate of Mitomycin C with Carboxymethyl-chitin," *Arch. Pract. Pharm.*, 1993, 53(3):141-147.
Souza et al., "Recombinant human granulocyte colony-stimulating factor: effects on normal and leukemic myeloid cells," *Science*, 1986, 232:61-65.
Soyez et al., "Biological evaluation of mitomycin C bound to a biodegradable polymeric carrier," *J. Controlled Release*, 1997, 47:71-80.
Spivak and Hogans, "The in Vivo Metabolism of Recombinant Human Erythropoietin in the Rat," *Blood*, 1989, 73:90-99.
Staros, "*N*-Hydroxysulfosuccinimide Active Esters: Bis(*N*-hydroxysulfosuccinimide) Esters of Two Dicarboxylic Acids Are Hydrophilic, Membrane-Impermeant, Protein Cross-Linkers," *Biochemistry*, 1982, 21:3950-3955.
Sunamoto and Iwamoto, "Protein-Coated and Polysaccharide-Coated Liposomes as Drug Carriers," *CRC Critical Review in Therapeutic Drug Carrier Systems*, 1986, 2:117-136.
Sytkowski et al., "Human erythropoietin dimers with markedly enhanced in vivo activity," *Proc. Natl. Acad. Sci. USA*, 1998, 95(3):1184-1188.
Sytkowski et al., "An Erythropoietin Fusion Protein Comprised of Identical Repeating Domains Exhibits Enhanced Biological Properties," *J. Biol. Chem.*, 1999, 274(35):24773-24778.
Takeuchi et al., "Relationship between sugar chain structure and biological activity of recombinant human erythropoietin produced in Chinese hamster ovary cells," *Proc. Natl. Acad. Sci. USA*, 1989, 86:7819-7822.
Takeuchi and Kobata, "Structures and functional roles of the sugar chains of human erythropoietins," *Glycobiology*, 1991, 1(4):337-346.
Tam et al., "Soluble Dextran-Hemoglobin Complex as a Potential Blood Substitute," *Proc. Natl. Acad. Sci. USA*, 1976, 73(6):2128-2131.
Tanaka et al., "Pharmacokinetics of recombinant human granulocyte colony-stimulating factor conjugated to polyethylene glycol in rats," *Cancer Research*, 1991, 51:3710-3714.
Thomas et al., "Measuring blood volume with fluorescent-labeled hydroxyethyl starch," *Crit. Care Med.*, 2000, 28(3):627-631.
Thomas, "Carbohydrate Binding Sites," *Meth. Enzymol.*, 1977, 46:362-368.
Thorpe et al., "Blockade of the galactose-binding sites of ricin by its linkage to antibody," *Eur. J. Biochem.*, 1984, 140:63-71.
Toyama et al., "Surface design of SPR-based immunosensor for the effective binding of antigen or antibody in the evanescent field using mixed polymer matrix," *Sensors and Actuators B*, 1998, 52:65-71.
De Velasco et al., "Synthetic Peptides Representing T-Cell Epitopes Act as Carriers in Pneumococcal Polysaccharide Conjugate Vaccines," *Infect. Immun.*, 1995, 63(3):961-968.
Van Patten et al., "Oxidation of Methionine Residues in Antithrombin," *J. Biol. Chem.*, 1999, 274(15):10268-10276.
Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.
Vilaseca et al., "Protein conjugates of defined structure: Synthesis and use of a new carrier molecule," *Bioconjugate Chemistry*, 1993, 4(6):515-520.
Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.
Weidler et al., "Pharmakokinetische Merkmale als Kriterien für den klinischen Einsatz von Hydroxyethylstärke," *Arzneim.-Forsch./Drug Res.*, 1991, 41:494-498 (w/English summary).
White and Kennedy, "Oligosaccharides," *Carbohydrate analysis: a practical approach*, 1996, Chaplin and Kennedy (eds.), Chapter 2, pp. 1-36.
Whitesides et al., "Rates of Thiol-Disulfide Interchange Reactions between Mono- and Dithiols and Ellman's Reagent," *J. Org. Chem.*, 1977, 42(2):332-338.

Wong et al., "Analysis of carbohydrate-protein interactions with synthetic N-linked neoglycoconjugate probes," *Biochem. J.*, 1993, 296:817-825.
Wong et al., "Synthetic glycosylation of proteins using *N*-(β-saccharide) iodoacetamides: applications in site-specific glycosylation and solid-phase enzymic oligosaccharide synthesis," *Biochem. J.*, 1994, 300:843-850.
Wong, *Chemistry of protein conjugation and cross-linking*, 1993, CRCS, Inc. (TOC only).
Xue and Wong; "Preparation of Conjugated Hemoglobins," *Meth. Enzymol.*, 1994, 231:308-322.
Yalpani et al., "Selective Chemical Modifications of Dextran," *J. Polymer Science: Polymer Chemistry Edition*, 1985, 23:1395-1405.
Yamaguchi et al., "Effects of site-directed removal of *N*-glycosylation sites in human erythropoietin on its production and biological properties," *J. Biol. Chem.*, 1991, 266(30):20434-20439.
Yoshida, "Glycamine Formation via Reductive Amination of Oligosaccharides with Benzylamine," *Meth. Enzymol.*, 1994, 247:55-64.
Zalipsky, "Functionalized Poly(ethylene glycol) for Preparation of Biologically Relevant Conjugates," *Bioconjugate Chem.*, 1995, 6:150-165.
Zara et al., "A Carbohydrate-Directed Heterobifunctional Cross-Linking Reagent for the Synthesis of Immunoconjugates," *Anal. Biochem.*, 1991, 194:156-162.
Zettlmeissl et al., "Characterization of Recombinant Human Antithrombin III Synthesized in Chinese Hamster Ovary Cells," *J. Biol. Chem.*, 1989, 264 (35):21153-21159.
Zhou et al., "Application of capillary electrophoresis, liquid chromatography, electrospray-mass spectrometry and matrix-assisted laserdesorption/ionization—time of flight—mass spectrometry to the characterization of recombinant human erythropoietin," *Electrophoresis*, 1998, 19(13):2348-2355.
Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.
Zucali and Sulkowski, "Purification of human urinary erythropoietin on controlled-pore glass and silicic acid," *Exp. Hematol.*, 1985, 13(3):833-837.
Adamczyk and Fishpaugh, "A Solid Supported Synthesis of Thiol Esters," *Tetrahedron Lett.*, 1996, 37(25):4305-4308.
Aly et al., "Hemophilia A due to mutations that create new N-glycosylation sites," *Proc. Natl. Acad. Sci. USA*, 1992, 89:4933-4937.
Andersson et al., "Isolation and characterization of human factor VIII: Molecular forms in commercial factor VIII: concentrate, cryoprecipitate, and plasma," *Proc. Natl. Acad. Sci. USA*, 1986, 83:2979-2983.
Armitage, "Emerging Applications of Recombinant Human Granulocyte-Macrophage Colony-Stimulating Factor," *Blood*, 1998, 92(12):4491-4508.
Balland et al., "Characterisation of two differently processed forms of human recombinant factor IX synthesised in CHO cells transformed with a polycistronic vector," *Eur. J. Biochem.*, 1988, 172(3):565-572.
Bauer and Rosenberg, "Role of Antithrombin III as a Regulator of In Vivo Hematol Coagulation," *Semin. Hematol.*, 1991, 28:10-18.
Berg et al., "Engineering the proteolytic specificity of activated protein C improves its pharmacological properties," *Proc. Natl. Acad. Sci. USA*, 2003, 100(8):4423-4428.
Bhattacharyya et al., "Recombinant Factor VIII for Haemophilia An Overview of Production Technologies," *CRIPS*, 2003, 4(3):2-8.
Björk and Danielsson, "Antithrombin and related inhibitors of coagulation proteinase," *Proteinase Inhibitors*, 1986, Chapter 17, pp. 489-513.
Boorsma et al., "Bioprocess Applications of a Sindbis Virus-Based Temperature-Inducible Expression System," *Biotech. Bioeng.*, 2002, 79(6): 602-609.
Carrell et al., "Human $\alpha_1$-antitrypsin: carbohydrate attachment and sequence homology," *FEBS Lett.*, 1981, 135(2):301-303.
Carver et al., "Expression of human α1 antitrypsin in transgenic sheep," *Cytotechnology*, 1992, 9:77-84.

Castillo et al., "Sensitive Substrates for Human Leukocyte and Porcine Pancreatic Elastase: A Study of the Merits of Various Chromophoric and Fluorogenic Leaving Groups in Assays for Serine Proteases," *Anal. Biochem.*, 1979, 99:53-64.

Cebon et al., "Granulocyte-Macrophage Colony Stimulating Factor from Human Lymphocytes. The effect of glycosylation on receptor binding and biological activity," *J. Biol. Chem.*, 1990, 268(8):4483-4491.

Chamow and Ashkenazi, *Antibody Fusion Proteins*, 1999, Wiley & Sons, Inc. (TOC Only).

Chan et al., "Preparation of O-esters from the corresponding thiol esters: *tert*-butyl cyclohexanecarboxylate," *Organic Syntheses, Coll.*, 1990, 7:87-93.

Chen et al., "Purification of $\alpha_1$ Proteinase Inhibitor from Human Plasma Fraction IV-1 by Ion Exchange Chromatography," *Vox Sang*, 1998, 74:232-241.

Choay et al., "Structural studies on a biologically active hexasaccharide obtained from heparin," *Ann. NY Acad. Sci.*, 1981, 370:644-649.

Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-499.

Colman, "Production of therapeutic proteins in the milk of transgenic livestock," *Biochem. Soc. Symp.*, 1998, 63:141-147.

Conradt et al., "Expression of Human Interleukin-2 in Recombinant Baby Hamster Kidney, Ltk-, and Chinese Hamster Ovary Cells. Structure of O-linked carbohydrate chains and their location within the polypeptide," *J. Biol. Chem.*, 1989, 264(29):17368-17373.

Corey and Clark, "A new method for the synthesis of 2-pyridinethiol carboxylic esters," *Tetrahedron Lett.*, 1979, 31:2875-2878.

de Koning et al., "An approach to the synthesis of peptide-PNA-peptide conjugates via native ligation," *Tetrahedron Lett.*, 2002, 43(45): 8173-8176.

Denzlinger et al., "Differential Activation of the Endogenous Leukotriene Biosynthesis by Two Different Preparations of Granulocyte-Macrophage Colony-Stimulating Factor in Healthy Volunteers," *Blood*, 1993, 81(8):2007-2013.

Donahue et al., "Effects of N-linked Carbohydrates on the In Vivo Properties of Human GM-CSF," *Cold Spring Harbor Symp. Quant. Biol.*, 1986, 51:685-692.

Ernst et al. (eds.), *Carbohydrates in Chemistry and Biology*, 2000, Part I, vol. 1-2, Whiley-VCH Weinheim (TOC only).

European Pharmacopoeia, 2001, 911-917.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271(5):907-919.

Franzen and Svensson, "Structural Studies on the Carbohydrate Portion of Human Antithrombin III," *J. Biol. Chem.*, 1980, 255(11):5090-5093.

Fujiki et al., "Studies on the disulfide bonds in human pituitary follicle-stimulating hormone," *Biochim. Biophys. Acta*, 1980, 624:428-435.

Goldstein and Gelb, "An alternate preparation of thioester resin linkers for solid-phase synthesis of peptide C-terminal thioacids," *Tetrahedron Lett.*, 2000, 41(16):2797-2800.

Goronzy et al., "T-Cell Derived Lymphokines as Regulators of Chronic Inflammation: Potential Targets for Immunomodulation?" *Am. J. Ther.*, 1996, 3(2):109-114.

Gribben et al., "Development of antibodies to unprotected glycosylation sites on recombinant GM-CSF," *Lancet*, 1990, 335:434-437.

Harris et al., "Pegylation. A novel process for modifying pharmacokinetics," *Clin. Pharmacokinet*, 2001, 40(7): 539-551.

He et al., "A simplified system for generating recombinant adenoviruses," *Proc. Natl. Acad. Sci. USA*, 1998, 95:2509-2514.

Hodges and Chan, "Locations of Oligosaccharide Chains in Human α1-Protease Inhibitor and Oligosaccharide Structures at Each Site," *Biochemistry*, 1982, 21:2805-2810.

Hodges et al., "Structure of the Oligosaccharide Chains in Human $\alpha_1$-Protease Inhibitor," *J. Biol. Chem.*, 1979, 254(17):8208-8212.

Hovgaard et al., "Clinical pharmacokinetic studies of a human haemopoietic growth factor, GM-CSF," *Eur. J. Clin. Inv.*, 1992, 22:45-49.

Hovinen et al., "Ethyl[2-deoxy-5-0-(4,4'-dimethoxytrityl)-α-and β-D-*erythro*-pentofuranosyl] acetates as versatile intermediates in nucleic acid chemistry," *Nucleosides Nucleotides*, 1999, 18:1263-1264.

Iakovenko et al., "Semi-synthetic Rab proteins as tools for studying intermolecular interactions," *FEBS Letters*, 2000, 468:155-158.

Ingenito et al., "Solid Phase Synthesis of Peptide C-Terminal Thioesters by Fmoc/*t*-Bu Chemistry," *J. Am. Chem. Soc.*, 1999, 121:11369-11374.

Jaques et al., "N.M.R. spectroscopy and calcium binding of sialic acids: N-glycolylneuraminic acid and periodate-oxidized N-acetylneuraminic acid," *Carb. Res.*, 1980, 83:21-32.

Karpusas et al., The crystal structure of human interferon β at 2.2-Å resolution, *Proc. Natl. Acad. Sci. USA*, 1997, 94:11813-11818.

Kaufman et al., "Synthesis, Processing, and Secretion of Recombinant Human Factor VIII Expressed in Mammalian Cells," *J. Biol. Chem.*, 1988, 263(13):6352-6362.

Kaushansky et al., "Role of Carbohydrate in the Function of Human Granulocyte-Macrophage Colony-Stimulating Factor," *Biochemistry*, 1987, 26:4861-4867.

Keene et al., "Expression of Biologically Active Human Follitropin in Chinese Hamster Ovary Cells," *J. Biol. Chem.*, 1989, 264(9):4769-4775.

Kochendoerfer et al., "Design and Chemical Synthesis of a Homogeneous Polymer-Modified Erythropoiesis Protein," *Science*, 2003, 299(5608):884-887.

Kraehenbuhl et al., "Preparation and characterization of an immunoelectron microscope tracer consisting of a heme-octapeptide coupled to Fab," *J. Exp. Med.*, 1974, 139:208-223.

Lahiri et al., "Antithrombin-Heparin Cofactor: An Inhibitor of Plasma Kallikrein," *Arch. Biochem. Biophys.*, 1976, 175:737-747.

Lapthorn et al., "Crystal structure of human chorionic gonadotropin," *Nature*, 1994, 369:455-461.

Li et al., "Direct preparation of peptide thioesters using an Fmoc solid-phase method," *Tetrahedron Lett.*, 1998, 39(47):8669-8672.

Lin et al., "L-Cysteine as a water-soluble cation scavenger in the removal of the 2,4,6-trimethoxybenzyl group from thiols," *Tetrahedron Lett.*, 2002, 43:4531-4533.

March, "Delocalized Chemical Bonding," *Adv. Org. Chem.*, 1992, 4th Edition, John Wiley and Sons, New York, Chapter 2 pp. 26-292.

Masamune et al., "A General, Selective 3695 Synthesis of Thiol Esters," *Can. J. Chem.*, 1975, 53:3693-3695.

Masuda et al., "Synthesis and Anti-Influenza Evaluation of Orally Active Bicyclic Ether Derivatives Related to Zanamivir," *Bioorganic & Medicinal Chemistry Letters*, 2003, 13:669-673.

Mega et al., "Studies on the Oligosaccharide Chains of Human $\alpha_1$-Protease Inhibitor. I. Isolation of glycopeptides," *J. Biol. Chem.*, 1980, 255(9):4053-4056.

Mega et al., "Studies on the Oligosaccharide Chains of Human $\alpha_1$-Protease Inhibitor. II. Structure of oligosaccharides," *J. Biol. Chem.*, 1980, 255(9):4057-4061.

Menache, "Antithrombin III: Introduction," *Semin. Hematol.*, 1991, 28:1-2.

Menache et al., "Antithrombin III: physiology, deficiency, and replacement therapy," *Transfusion*, 1992, 32:580-588.

Ming et al., "Interleukin 6 is the Principal Cytolytic T Lymphocyte Differentiation Factor for Thymocytes in Human Leukocyte Conditioned Medium," *J. Mol. Cell. Immunol.*, 1989, 4:203-212.

Moonen et al., "Increased biological activity of deglycosylated recombinant human granulocyte/macrophage colony-stimulating factor produced by yeast or animal cells," *Proc. Natl. Acad. Sci. USA*, 1987, 84:4428-4431.

Mori et.al., "The Activation of Type 1 and Type 2 Plasminogen by Type I and Type II Tissue Plasminogen Activator," *J. Biol. Chem.*, 1995, 270(7):3261-3267.

Muir et al., "Expressed protein ligation: A general method for protein engineering," *Proc. Natl. Acad. Sci. USA*, 1998, 95:6705-6710.

Mumberg et al., "Regulatable promoters of *Saccharomyces cerevisiae*: comparison of transcriptional activity and their use for heterologous expression," *Nucl. Acids Res.*, 1994, 22(25):5767-5768.

Murano et al., "Some properties of antithrombin-III and its concentration in human plasma," *Thromb. Res.*, 1980, 18:259-262.

Ohta et al., "Usefulness of Glycopeptide Mapping by Liquid Chromatography/Mass Spectrometry in Comparability Assessment of Glycoprotein Products," *Biologicals*, 2002, 30(3):235-244.

Okamoto et al., "Purification and Characterization of Three Forms of Differently Glycosylated Recombinant Human Granulocyte-Macrophage Colony-Stimulating Factor," *Arch. Biochem. Biophys.*, 1991, 286(2):562-568.

Olson et al., "Role of the Antithrombin-binding Pentasaccharide in Heparin Acceleration of Antithrombin-Proteinase Reactions. Resolution of the antithrombin conformational change contribution to heparin rate enhancement," *J. Biol. Chem.*, 1992, 267(18):12528-12538.

Olson and Björk, "Predominant Contribution of Surface Approximation to the Mechanism of Heparin Acceleration of the Antithrombin-Thrombin Reaction. Elucidation from salt concentration effects," *J. Biol. Chem.*, 1991, 266(10):6353-6364.

Opal et al., "Antithrombin, heparin, and heparan sulfate," *Crit. Care Med.*, 2002, 30(5):S325-S331.

Pelter et al., "Synthesis of Thioesters by Reactions of Carboxylic Acids with Tris-(ethylthio)borane," *J. Am. Chem. Soc., Perkin Trans I*, 1977, 1672-674.

Peterson, *The Physiological Inhibitions of Blood Coagulation and Fibrinolysis*, 1979, Elsevier/North-Holland Biomedical Press, p. 43.

Pike et al., "Heparin-dependent Modification of the Reactive Center Arginine of Antithrombin and Consequent Increase in Heparin Binding Affinity," *J. Biol. Chem.*, 1997, 272_32:19652-19655.

Ragnhammar et al., "Induction of Anti-Recombinant Human Granulocyte-Macrophage Colony-Stimulating Factor (*Escherichia coli*-Derived) Antibodies and Clinical Effects in Nonimmunocompromised Patients," *Blood*, 1994, 84(12):4078-4087.

Rapoport et al., "Protein transport across the eukaryotic endoplasmic reticulum and bacterial inner membranes," *Annu. Rev. Biochem.*, 1996, 65:271-303.

Reddy et al., "Use of peginterferon alfa-2a (40 KD) (Pegasys®) for the treatment of hepatitis C," *Advanced Drug Delivery Reviews*, 2002, 54:571-586.

Reischl (ed)., *Molecular Diagnosis of Infectious Diseases*, 1997, vol. 13, Totowa NJ, Humana Press Inc. (TOC Only).

Revoltella et al., "Natural and Therapy-Induced Anti-GM-CSF and Anti-G-CSF Antibodies in Human Serum," *Leukemia and Lymphoma*, 1997, 26:29-34.

Roemisch et al., "Antithrombin: a new look at the actions of a serine protease inhibitor," *Blood Coagul. Fibrinolysis*, 2002, 13:657-670.

Rosenberg, "Role of heparin and heparinlike molecules in thrombosis and atherosclerosis," *Fed. Proc.*, 1985, 44:404-409.

Rosenberg et al., "Antithrombin-III," *Rev. Hematol.*, 1986, 2:351-416.

Schlesinger, "Alphaviruses—vectors for the expression of heterologous genes," *Trends Biotech.*, 1993, 11:18-22.

Schröter et al., "Male-specific Modification of 29 Human CD52," *J. Biol. Chem.*, 1999, 274(42):29862-29873.

Shin et al., "Fmoc-Based Synthesis of Peptide-$\alpha$Thioesters: Applications to the Total Chemical Synthesis of a Glycoprotein by Native Chemical Ligation," *J. Am. Chem. Soc.*, 1999, 121:11684-11689.

Spellman et al., "Carbohydrate Structures of Human Tissue Plasminogen Activator Expressed in Chinese Hamster Ovary Cells," *J. Biol. Chem.*, 1989, 264(24):14100-14111.

Stetsenko and Gait, "Efficient Conjugation of Peptides to Oligonucleotides by "Native Ligation," *J. Org. Chem.*, 2000, 65:4900-4908.

Stewart et al., "Identification of the Mechanism Responsible for the Increased Fibrin Specificity of TNK-Tissue Plasminogen Activator Relative to Tissue Plasminogen Activator," *J. Biol. Chem.*, 2000, 275(14):10112-10120.

Tebbutt, "Technology evaluation: transgenic $\alpha$-1-antitrypsin (AAT), PPL Therapeutics," *Curr. Opin. Ther.*, 2000, 2(2):199-204.

Thim et al., "Amino Acid Sequence and Posttranslational Modification of Human Factor VII$_a$ from Plasma and Transfected Baby Hamster Kidney Cells," *Biochemistry*, 1988, 27:7785-7793.

Toole et al., "Molecular cloning of a cDNA encoding human antihaemophilic factor," *Nature*, 1984, 312:342-347.

Travis and Salvesen, "Human plasma proteinase inhibitors," *Ann. Rev. Biochem.*, 1983, 52:655-709.

Veronese et al., "Peptide and Protein PEGylation—A Review of Problems and Solutions," *Biomaterials*, 2001, 22(5):405-417.

Wadhwa et al., "Immunogenicity of Granulocyte-Macrophage Colony-Stimulating Factor (GM-CSF) Products in Patients Undergoing Combination Therapy with GM-CSF," *Clin. Cancer Res.*, 1999, 5:1351-1361.

Watanabe et al., "A facile synthesis of carboxylic thiol esters from carboxylic acids and thiols," *Chem. Lett.*, 1976, 741-742.

Weisshaar et al., "NMR investigations of the N-linked oligosaccharides at individual glycosylation sites of human lutropin," *Eur. J. Biochem.*, 1991, 195:257-268.

Wright et al., "High level expression of active human alpha-1-antitrypsin in the milk of transgenic sheep," *Biotechnology*, 1991, 9:830-834.

Yoshitake et al., "Nucleotide Sequence of the Gene for Human Factor IX (Antihemophilic factor B)," *Biochemistry*, 1985, 24:3736-3750.

Definition of dimethyl sulfoxide, the Merck Index, 2006, Merck & Co., 14th edition, accessed online http://themerckindex.cambridgesoft.com/TheMerckIndex/index.asp on Sep. 4, 2007.

Dieterich et al., "Hydroxyethyl Starch Antibodies in Humans: Incidence and Clinical Relevance," *Anesth. Analg.*, 1998, 86:1123-1126.

Cera et al., "Water-soluble polysaccharide-anthracycline conjugates: Biological Activity," *Anti-Cancer Drug Design*, 1992, 7(2):143-151.

Gaucher et al., "Stereospecific synthesis and characterization of aminoglycoside ligands from diethylenetriamine," *J. Organic Chem.*, 1999, 64:4012-4015.

Guillaumie et al., "Immobilization of pectin fragments on solid supports: Novel coupling by thiazolidine formation," *Bioconjugate Chem.*, 2002, 13:285-294.

Liu et al., "Characterization of the structural and functional changes of hemoglobin in dimethyl sulfoxide by spectroscopic techniques," *Biochim. Biophys. Acta*, 1998, 138:53-60.

Okamoto et al., "A facile incorporation of the aldehyde function into DNA: 3-formylindole nucleoside as an aldehyde-containing universal nucleoside," *Tetrahedron Lett.*, 2002, 43:4581-4583.

Radomsky and Temeriusz, "Thiazolidine-4(R)-carboxylic acids derived from sugars: part I, C-2-epimerisation in aqueous solutions," *Carb. Res.*, 1989, 187:223-237.

Shao and Tam, "Unprotected peptides as building blocks for the synthesis of peptide dendrimers with oxime, hydrazone and thiazolidine linkages," *J. Am. Chem. Soc.*, 1995, 117(14):3893-3899.

Yang et al., "Functional changes of carboxymethyl potato starch by conjugation with amino acids," *Biosci. Biotechnol. Biochem.*, 1995, 59(12):2203-2206.

Anderson and Meister, "Inhibition of $\gamma$-glutamyl transpeptidase and induction of glutathionuria by $\gamma$-glutamyl amino acids," *Proc. Natl. Acad. Sci. USA*, 1986, 83:5029-5032.

Dorner et al., "Increased Synthesis of Secreted Proteins Induces Expression of Glucose-regulated Proteins in Butyrate-treated Chinese Hamster Ovary Cells," *J. Biol. Chem.*, 1989, 264(34):20602-20607.

Luo et al., "Controlled DNA delivery systems," *Pharm. Res.*, 1999, 16(8):1300-1308.

Masamune et al., "Tylonolide hemiacetal, the aglycone of tylosin, and its partial synthesis," *J. Am. Chem. Soc.*, 1976, 98(24):7874-7875.

Mukaiyama et al., "Peptide Synthesis via Oxidation-Reduction Condensation by the Use of Non-metallic Compound as a Mercaptan Scavenger," *Bull. Chem. Soc. Jpn.*, 1970, 43:1271.

Somogyi, "Determination of reducing sugars," *Meth. Carb. Chem.*, 1962, 1:384-386.

Ubeda and Habener, "The large subunit of the DNA replication complex C (DSEB/RF-C140) cleaved and inactivated by caspase-3 (CPP32/YAMA) during Fas-induced apoptosis," *J. Biol. Chem.*, 1997, 272(31):19562-19568.

Wasley et al., "The Importance of N- and O-Linked Oligosaccharides for the Biosynthesis and In Vitro and In Vivo Biologic Activities of Erythropoietin," Blood, 1991, 77(12):2624-2632.
Cervigni et al., "Synthesis of Glycopeptides and Lipopeptides by Chemoselective Ligation," Angewandte Chemie International Edition in English, 1996, 35(11):1230-1232.
Lee and Park, "Conjugation of trypsin by temperature-sensitive polymers containing a carbohydrate moiety: thermal modulation of enzyme activity," Biotechnol. Prog., 1998, 14(3):508-516.
Dictionary of Chemistry and Chemical Technology, 2003, p. 769.
Axèn et al., "Chemical Coupling of Peptides and Proteins to Polysaccharides by Means of Cyanogen Halides," Nature, 1967, 214:1302-1304.
Tam et al., "Peptide Synthesis Using Unprotected Peptides Through Orthogonal Coupling Methods," Proc. Natl. Acad. Sci. USA, 1995, 92:12485-12489.
Pierce Chemical Technical Library, "cross-linking," 1994, 45 pages.
Carey and Sundberg, "Organische Chemie," VCH Verlagsgesellschaft mbH, Weinheim (DE), 1995, pp. 432-433 and 455.
Peri et al., "Chemo- and Stereoselective Glycosylation of Hydroxylamino Derivatives: A Versatile Approach to Glycoconjugates," Tetrahedron, 1998, 54:12269-12278.
Heindel et al., "Hydrazide Pharmaceuticals as Conjugates to Polyaldehyde Dextran: Syntheses, Characterization, and Stability," Bioconj. Chem., 1990, 1:77-82.
Wilchek and Bayer, "Labeling Glycoconjugates with Hydrazide Reagents," Meth. Enzymol., 1987, 138:429-442.
Anno et al., "Sugar Chemistry," 1995, p. 31.
Lund et al., "Assessment of methods for covalent binding of nucleic acids to magnetic beads, Dynabeads™, and the characteristics of the bound nucleic acids in hybridization reactions," Nucl. Acids Res., 1988, 16(22):10861-10880.
Wang et al., "Delivery of Antisense Oligonucleotides Using HPMA Polymer: Synthesis of A Thiol Polymer and Its Conjugation to Water-Soluble Molecules," Bioconj. Chem., 1998, 9:749-757.
Stille and Dittmann, "Atherosclerosis as Consequence of Chronic Infection by Chlamydia Pneumoniae," Herz, 1998, 23:185-192.
Bayer et al., "The Avidin-Biotin Complex in Affinity Cytochemistry," Meth. Enzymol., 1979, 62:308-315.
Boyer et al., "Reaction in Biphasic Water/Organic Solvent System in the Presence of Surfactant: Inverse Phase Transfer Catalysis versus Interfacial Catalysis," Tetrahedron, 2000, 56:303-307.
Heitzmann and Richards, "Use of the Avidin-Biotin Complex for Specific Staining of Biological Membranes in Electron Microscopy," Proc. Natl. Acad. Sci. USA, 1974, 71(9):3537-3561.
Lewis et al., "The phase transfer catalysed synthesis of isoflavone-O-glucosides," J. Chem. Soc. Perkins Trans. 1, 1998, pp. 2481-2484.
Lewis and Wähälä, "Regiospecific 4'-O-β-glucosidation of isoflavones," Tetrahedron Letters, 1998, 39(51):9559-9562.
Organikum, Organisch-chemisches Grundpraktikum, 1984, VEB Deutscher Verlag der Wissenschaften, p. 472.
Wong, Chemical Dictionary Entry Concerning Carbohydrates, Chemistry of Protein Conjugation and Cross-Linking, 1993, CRCS, Inc., 6 pages including English-language Abstract.
Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.
Schmoll et al. (eds.), "Summary of Basics of Oncology and Current Therapeutic Approaches," Compendium for Internistic Oncology, 1996, Table of Contents with English Summary.
Sommermeyer et al., "Hydroxyethylstarch for Clinical Application: Physical and Chemical Characterisation," Krankenhauspharmazie, 1987, 8:271-278.
Klimek et al., "Specific Immunotherapy (Hyposensibilisation)," Allergologie and Umweltmedizin, Chapter 15, pp. 157-195, 1997.
Staab, "New Methods in Preparatory Organic Chemistry IV. Synthesis using heterocyclic amides (azolides)" Angew. Chem., 1962, 74(12):407-422.
Caliceti et al., "Immunological properties of uricase conjugated to neutral soluble polymers," Bioconjugate Chem., 2001, 12:515-522.
Dorwald, Side Reactions in Organic Synthesis, A Guide to Successful Synthesis Design, 2005 published by Wiley-VCH Verlag GmbH & Co., preface pp. IX-X.
Grieco et al., "Aryl selenocyanates and aryl thiocyanates: reagents for the preparation of activated esters," J. Org. Chem., 1978, 43(6):1283-1285.
"Heterobifunctional crosslinkers," Molecular Biosciences, Nov. 2001, retrieved Jun. 6, 2011 [http://www.molbio.com/Heterobi.htm].
"Oxime" from McGraw-Hill's Access Science, retrieved May 9, 2011 [http://accessscience.com/content.aspx?searchStr=oxime&id=480600].
"Crosslinking agents," Pierce Company, retrieved Aug. 25, 2011 [http://www.piercenet.com/browse.cfm?fldID=0203].
Reischl (ed)., Molecular Diagnosis of Infectious Diseases, 1997, vol. 13, Humana Press Inc., Totowa NJ (TOC Only).
Riess, "Oxygen carriers ('blood substitutes')—raison d'etre, chemistry, and some physiology," Chern. Rev., 2001, 101:2797-2919.
Svenson et al., "Oligosaccharide-protein conjugate: A novel approach for making Salmonella O- antigen immunogens," FEMS Microbiology Letters, 1977, 1:145-148.
Alagon et al., "Activation of Polysaccharides with 2-Iminothiolane and its Uses", Biochem. 19:4341-4345 (1980).
Balazy et al., "S-Nitroglutathione, a Product of the Reaction between Peroxynitrite and Glutathione That Generates Nitric Oxide", J. Biol. Chem. 273(48):32009-32015 (1998).
Etrych et al., "New HPMA Copolymers containing doxorubicin bound via pH-sensitive linkage: synthesis and preliminary in vitro and in vivo biological properties", Journal of Controlled Release 73:89-102 (2001).
European Pharmacopoeia, Supplemental 2001, "Haemodialysis Solutions" pp. 911-918.
Ganson et al., "Control of Hyperuricemia in Subjects with refractory gout, and induction of antibody against poly (ethylene glycol) (PEG), in a phase I trial of subcutaneous PEGylated urate oxidase", Arthritis Research & Therapy, 8: R12 (2005).
Glederblom et al., "Cremophor EL: the drawbacks and advantages of vehicle selection for drug formulation", European Journal of Cancer, 37:1590-1598 (2001).
Gerwech et al., "Tumor pH controls the in vivo efficacy of weak acid and base chemotherapeutics", Mol. Cancer Ther. 5(5):1275-1279 (2006).
Greenwald et al., "Drug Delivery Systems: Water Soluble Taxol 2'-Poly(ethylene glycol) Ester Prodrugs—Design and in Vivo Effectiveness" J. Med. Chem., 39:424-431 (1996).
Hamilton et al., "Characterization of a Human Ovarian Carcinoma Cell Line (NIH:OVCAR-3) with Androgen and Estrogen Receptors", Cancer Research, 43:5379-5389 (1983).
Jungheinrich et al., "Pharmacokinetics of Hydroxyethyl Starch", Clin Pharmacokinet, 44(7):681-699 (2005).
Katsumi et al., "Development of Polyethylene Glycol-Conjugated Poly-S-Nitrosated Serum Albumin, a Novel S-Nitrosothiol for Prolonged Delivery of Nitric Oxide in the Blood Circulation in Vivo", Journal of Pharmacology and Experimental Therapeutics, 314(3):1117-1124 (2005).
Kinstler et al., "Characterization and Stability of N-terminally PEGylated rhG-CSF", Pharmaceutical Research, 13(7):996-1002 (1996).
Kulicke et al., "Measurements of the Refractive Index Increment on Hydroxyethyl Starch as a Basis for Absolute Molecutlar Weight Determinations", Starch, 43(10):392-396 (1991).
Laine et al., "Polyethylene Glycol Nephrotoxicity secondary to prolonged High-Dose Intravenous Lorazepam", Annals of Pharmacotherapy, 29:1110-1114 (1995).
Bernardes et al., "The Direct Formation of Glycosyl Thiols from Reducing Sugars Allows One-Pot Protein Glycoconjugation", Angew. Chem. 118:4111-4115 (2006).
Besheer et al., "Enzymatically Catalyzed HES Conjugation Using Microbial Transglutaminase:Proof of Feasibility", Journal of Pharmaceutical Sciences, 98(11):4420-4428 (2009).
Lee et al., "Functional Polymers for Layer-by-Layer Construction of Multilayer via Chemoselective Immobilization", Macromolecules, 37:1849-1856, (2004).

Lieber et al., "A Continuous Tumor-Cell Line From a Human Lung Carcinoma with Properties of Type II Alveolar Epithelial Cells", Int. J. Cancer, 17:62-70, (1976).

Lipke et al., "Localized Delivery of Nitric Oxide from Hydrogels Inhibits Neointima Formation in Rat Cartoid Ballon Injury Model", Acta Biomaterialia, 1:597-606, (2005).

Megson et al., "Inhibition of Human Platelet Aggregation by a Novel S-Nitrosothiol is Abolished by Haemoglobin and Red Blood Cell in vitro: Implications for Anti-Thrombotic Therapy", British Journal of Pharmacology, 131:1391-1398, (2000).

Nathan et al., "Strategies for Covalent Attachment of Doxorubicin to Poly(PEG-Lys), a New Water Soluble Poly(ether urethane)", Journal of Bioactive and Compatible Polymers, 9:239-251 (1994).

Naundorf et al., "Characterization of two human mammary carcinomas, MT-1 and MT-3, suitable for in vivo testing of either lipids and their dirivatives", Breast Cancer Research and Treatment, 23:87-95, (1992).

Ph. Eur. Nachtrag, "Erythropoietini solutio concentrata", pp. 780, (2000).

Ph. Eur. Nachtrag, "Erythropoietini solutio concentrata", pp. 911, (2001).

Pharmeuropa, "erythropoietin Concentrated Solution", 8(3):371. (1996).

Thermo Scientific Pierce "Crosslinking Technical Handbook", 48pgs. (2009).

Reynolds et al., "S-nitrosohemoglobin deficiency: A mechanism for loss of physiological activity in banked blood", PNAS, 104(43):17058-17062, (2007).

Rodrigues et al., "Correlation of the acid-sensitivity of polyethylene glycol daunorubicin conjugates with their in vitro antiproliferative activity", Bioorganic & Medicinal Chemistry, 14:4110-4117, (2006).

Salo et al., "Aminooxy Functionalized Oligonucleotides: Preparation, On-Support Derivatization, and Postsynthetic Attachment to Polymer Support", Bioconjugate Chem., 10:815-823, (1999).

Schneerson et al., "Preparation, characterization and immunogenicity of haemophilus influenzae type b polysaccharide-protein conjugates", Journal of Experimental Medicine, 152:361-376 (1980).

Skopp et al., "Fingerprinting of proteins cleaved in solution by cyanogen bromide", Appl. and Theoret. Electrophoresis, 1:61-64, (1989).

Skwarczynski et al., "Paclitaxel Prodrugs Toward Smarter Delivery of Anticancer Agents", Journal of Medicinal Chemistry, 49(25):7253-7269, (2006).

Stien et al., "Development and characterisation of novel human multidrug resistant mammary carcinoma lines in vitro and in vivo", Int. J. Cancer, 72:885-891, (1997).

Tomasik et al., "Chemical Modification of Starch", Advaces in Carbohydrate Chemistry and Biochemistry, 59:179-403, (2004).

Velasco et al., "Synthetic Peptides Representing T-Cell Epitopes Act as Carriers in Pneumococcal Polysaccharide Conjugate Vaccines", Infection and Immunity, 63(3):961-968, (1995).

Vasey et al., :Phase I Clinical and Pharmacokinetic Study of PKI [N-(2-Hydroxypropyl)methacrylamide Copolymer Doxorubicin]: First Member of a New Class of Chemotherapeutic Agents-Drug-Polymer Conjugates, Clinial Cancer Research, 5:83-94, (1999).

Waltzinger et al., "Pharmacokinetics and Tolerability of a New Hydroxyethyl Starch (HES) Specification [HES (130/0.4)] after Single-Dose Infusion of 6% or 10% Solutions in Healthy Volunteers", Pharmacokinetics, 16(2):151-160, (1998).

Carrell et al., "Structural mobility of antithrombin and its modulation by heparin," Thromb Haemost., 1997, 78(1):516-519.

Cavallaro et al., "Folate-mediated targeting of polymeric conjugates of gemcitabine," Int. J. Pharmaceutics, 2006, 307:258-269.

Grieco et al., "Favored Reduction of α-Chlorosilanes vs. α-Chloroalkanes with Tri-n-butyltin Hydride," J.Org.Chem, 1978, 43(6):1285.

Harada, et al. "Carrier and dose effects on the pharmacokinetics of T-0128, a camptothecin analogue-carboxymethyl dextran conjugate, in non-tumor-and-tumor-bearing rats," J. Controlled Release, 2001, 71:71-86.

Harada, et al., "Determinants for the drug release from T-0128, camptothecin analogue-carboxymethyl dextran conjugate," J. Controlled Release, 2000, 69: 399-412.

Lee, Ed., Peptide and Protein Drug Delivery, Marcel Dekker, 1991, p. 65.

Pasut et al., "Antitumoral activity of PEG-gemcitabine prodrugs targeted by folic acid," J. Controlled Release, 2008, 127(3):239-248.

Peluso et al., "Asparagine surrogates for the assembly of N-linked glycopeptide mimetics by chemoselective ligation," Tetrahedron Lett., 2001, 42:2085-2087.

Rotondaro et al., "Purification and Characterization of Two Recombinant Human Granulocyte Colony-Stimulating Factor Glycoforms." Molecular Biotechnology, 1999, 11: 117-128.

Seymour et al., "A phase 1 study of BAY 38-3441 given as a short infusion daily for five days every 3 weeks. A National Cancer Institute of Canada Clinical Trials Groups Study," Eur. J. Cancer, 2001, 37(1): 73.

Svenson and Lindberg, "Coupling of Acid Labile Salmonella Specific Oligosaccharides to Macromolecular Carriers," J. Immunolog. Meth., 1979, 25: 323-335.

Svenson, "Immunochemistry of Salmonella O-Antigens: Preparation of an Octasaccharide-Bovine Serum Albmin Immunogen Representative of Salmonella Serogroup B O-Antigen and Characterization of the Antibody Response," J. Immunol., 1978, 120(5): 1750-1757.

Zhang, L. et al. "Thiazolidine formation as a general and site-specific conjugation method . . ." Anal. Biochem. (1996) vol. 233, pp. 87-93.

Orlando, "Modification of proteins and low molecular weight substances with hydroxyethyl starch (HES)," PhD Dissertation Paper, Justus-Liebig Universitat Giessen, 2003, 191 pages.

Gelbrich, "Untersuchungen zur Synthese neuartiger Cellulosematerialien durch topochemische Polymerreaktionen an mikrokristallinen Cellulosen," PhD Dissertation Paper, Vom Fachbereich Gelbrich. "Untersuchungen zur Synthese neuartiger Cellulosematerialien durch topochemische Polymerreaktionen an mikrokristallinen Cellulosen," PhD Dissertation Paper, Vom Fachbereich Chemie, der Technischen Universitat Darmstadt, 1999, 157 pages (English abstract included).

Blackburn and Gait, Eds., "DNA and RNA Structure,": in Nucleic Acids in Chemistry and Biology, 2nd Edition, 1996, Oxford University Press, pp. 15-81.

Englisch and Gauss, "Chemically modified oligonucleotides as probes and inhibitors," Angew Chem. Int. Ed. Engl., 1991, 30:613-29.

Lonngren et al., "Aldonate Coupling, A Simple Procedure for the Protein Conjugates for Studies of Carbohydrate-Binding Proteins," Arch. of BioChem. And BioPhys., 1976, 175:661-669.

Ng et al., "Pegaptanib, a targeted anti-VEGF aptamer for ocular vascular disease," Nature Reviews 2005, 5:123-126.

Nielsen et al., "Sequence-selective recognition of DNA by strand displacement with a thymidine-substituted polyamide," Science, 1991, 254:1497-1500.

Pieve et al., "Modification of thiol functionalized aptamers by conjugation of synthetic polymers," Bioconjugate Chemistry, 2012, 21:169-174.

Stille et al., "Atherosclerosis as Consequence of Chronic Infection by Chlamydia Pneumoniae," Herz, 1998, 23:185-192 (w/English summary, p. 186).

Ersdal-Badju et al., "Identification of the Antithrombin III Heparin Binding Site," J. Biol. Chem,. 1997, 272(31):19393-19400.

* cited by examiner ic reaction, of the hydroxyalkylstarch molecule and a functional group, which is able to react with this aldehyde group or functional group derived therefrom of the hydroxyalkylstarch molecule, of the low molecular weight substance, where the bonding resulting directly in the coupling reaction can be modified where appropriate by a further reaction to give the abovementioned covalent bonding.

COUPLING LOW-MOLECULAR SUBSTANCES TO A MODIFIED POLYSACCHARIDE

This application is a National Stage application under 35 U.S.C. §371 of International Application No. PCT/EP03/02084 having an International Filing Date of Feb. 28, 2003, which claims the benefit of priority of German PATENT APPLICATION Serial No. 10209822.0 having a filing date of Mar. 6, 2002.

There is a large number of low molecular weight substances of commercial interest, especially active pharmaceutical ingredients and crop protection agents, whose use is limited or even prevented by unsatisfactory solubility properties in an aqueous medium and/or short residence time in the body. Thus, for example, small pharmaceutical molecules are frequently removed from the circulation again too quickly by glomerular filtration in the kidney (exclusion limit about 70 kD), so that continual replenishment, which is costly and inconvenient for the patient, with this medicament is necessary, e.g. by frequently repeated administrations or infusion.

In order to avoid this disadvantage, in some cases slightly soluble active pharmaceutical ingredients are administered as an oily bolus which frequently forms painful deposits at the injection site. In addition, the use of such slightly soluble medicaments is often associated with toxic side effects because of their deposition in organs such as liver and/or kidney. Such unwanted side effects in turn result in the concentration range which can be employed in vivo for the active ingredient being greatly restricted.

An approach followed in recent times for eliminating the described problems consists of coupling such problematic substances to readily soluble biocompatible polymers such as, for example, polyethylene glycol and dextran. It is possible through the coupling on the one hand to increase the molecular weight above the threshold of 70 kD, so that the plasma residence time of smaller molecules can be drastically increased, and on the other hand the solubility in aqueous medium can be improved by the hydrophilic polymer portion.

Most modifications to date have been carried out with polyethylene glycol or dextran, with PEG being generally preferred because it yields simpler products. Dextran conjugates often show high allergenicity, a low metabolic stability and, in many cases, low yields of the coupling reactions. There have likewise been reports of unpleasant or hazardous side effects such as pruritus, hypersensitivity reactions and pancreatitis on use of PEG conjugates. In addition, the biological activity of the active ingredients is more often greatly reduced in some cases after the PEG coupling. Moreover, the metabolism of the degradation products of PEG conjugates is still substantially unknown and possibly represents a health risk.

Thus, there is still a need for physiologically well tolerated alternatives to dextran or PEG conjugates, with which the solubility of poorly soluble low molecular weight substances can be improved and/or the residence time of low molecular weight substances in the plasma can be increased, resulting in improved pharmacodynamic properties of the active molecule.

It is therefore an object of the invention to provide such alternatives and to develop simple and efficient methods for preparing such alternative conjugates.

It has surprisingly been found that this object can be achieved by hydroxyalkylstarch conjugates which are characterized in that the binding interaction between the hydroxyalkylstarch molecule and the low molecular weight substance is based on a covalent bonding which is the result of a coupling reaction between the terminal aldehyde group, or a functional group derived from this aldehyde group by chemical reaction, of the hydroxyalkylstarch molecule and a functional group, which is able to react with this aldehyde group or functional group derived therefrom of the hydroxyalkylstarch molecule, of the low molecular weight substance, where the bonding resulting directly in the coupling reaction can be modified where appropriate by a further reaction to give the abovementioned covalent bonding.

The invention further includes pharmaceutical compositions which comprise these conjugates, and the use of these conjugates and compositions for the prophylactic or therapeutic treatment of the human or animal body, and methods for preparing these conjugates and compositions.

The hydroxyalkylstarch (HAS) employed according to the invention can be prepared by a known method, e.g. hydroxyalkylation of starch at the $C_2$ and/or $C_6$ position of the anhydroglucose units with alkylene oxide or 2-chloroalkanol, e.g. 2-chloroethanol (see, for example, U.S. Pat. No. 5,218,108 for the hydroxyethylation of starch), with various desired molecular weight ranges and degrees of substitution. It is also possible to employ any preparations obtainable commercially. The definition of the alkyl grouping in "hydroxyalkylstarch", as used herein, includes methyl, ethyl, isopropyl and n-propyl, with particular preference for ethyl. A substantial advantage of hydroxyethylstarch (HES) is that it is already approved by the authorities as biocompatible plasma expander and is employed clinically on a large scale.

The average molecular weight of the hydroxyalkylstarch can be in the range from about 3 kD to several million daltons, preferably about 10 kD to about 200 kD, more preferably in the range from about 70 kD to about 1000 kD, particularly preferably about 130 kD. To increase the residence time of the low molecular weight substance in the organism, the average molecular weight of the hydroxyalkylstarch is preferably chosen so that the glomerular threshold of 70 kD is exceeded with the conjugates. The degree of substitution (ratio of the number of modified anhydroglucose units to the number of anhydroglucose units in total) may likewise vary and will frequently be in the range from about 0.2 to 0.8, preferably about 0.3 to 0.7, more preferably about 0.5. (Note: the numbers relate to the "degree of substitution", which is between 0 and 1). The ratio of $C_2$ to $C_6$ substitution is normally in the range from 4 to 16, preferably in the range from 8 to 12.

These parameters can be adjusted by known methods. Experience with the use of hydroxyethylstarch as blood substitute has shown that the residence time of HES in the plasma depends on the molecular weight and the degree of substitution and type of substitution ($C_2$ substitution or $C_6$ substitution), with a higher molecular weight, a higher degree of substitution and a higher proportion of $C_2$ substitution increasing the residence time.

These relationships also apply to the inventive conjugates of hydroxyalkylstarch and low molecular weight substances, so that the residence time of a particular conjugate in the plasma can be adjusted via the proportion of polysaccharide.

As already mentioned, the functional group involved in the coupling reaction of the hydroxyalkylstarch molecule is the terminal aldehyde group or a functionality derived therefrom by chemical reaction.

One example of such a chemical reaction is the selective oxidation of this aldehyde group with a suitable oxidizing agent such as, for example, iodine, bromine or some metal ions, or else by means of electrochemical oxidation to a carboxyl group or activated carboxyl group, e.g. an ester, lactone, amide, with the carboxyl group being converted where appropriate in a second reaction into the activated derivative. This carboxyl group or activated carboxyl group can then be coupled to a primary amino or thiol group of the low molecular weight substance to form an amide linkage or thioester linkage. A further possibility is coupling to a hydroxyl function of the low molecular weight substance to form an ester.

An inventive conjugate can, however, also be obtained by reacting the low molecular weight substance with a suitable physiologically tolerated bifunctional linker molecule to introduce a desired functional group. The remaining reactive group of the coupled-on linker molecule is likewise for the purposes of the present invention considered to be a "reactive functional group of the low molecular weight substance".

Suitable linker molecules comprise at one end a grouping able to enter into a covalent bonding with a reactive functional group of the low molecular weight substance, e.g. an amino, thiol, carboxyl or hydroxy group, and at the other end a grouping likewise able to enter into a covalent bonding with the terminal aldehyde group or a functional group derived therefrom by chemical reaction, e.g. a carboxyl group, activated carboxyl group, amino or thiol group.

Between the two functional groups of the linker molecule there is a biocompatible bridging molecule of suitable length, e.g. a grouping derived from an alkane, an (oligo)alkylene glycol grouping or another suitable oligomer grouping. Preferred groupings able to react with amino groups are, for example, N-hydroxysuccinimide esters, sulfo-N-hydroxysuccinimide esters, imido esters or other activated carboxyl groups; preferred groupings able to react with thiol groups are, for example, maleimide and carboxyl groups; preferred groupings able to react with aldehyde or carboxyl groups are, for example, amino or thiol groups.

Examples of linker molecules for connecting SH and NH functions are:

| AMAS | (N-α(maleimidoacetoxy)succinimide ester) |
| BMPS | (N-β(maleimidopropyloxy)succinimide ester) |
| GMBS | (N-γ(maleimidobutyryloxy)succinimide ester) |
| EMCS | (N-ε(maleimidocaproyloxy)succinimide ester) |
| MBS | (m-(maleimidobenzoyl)-N-hydroxysuccinimide ester) |
| SMCC | (succinimidyl 4-(N-maleimidomethyl)cyclohexane-1-carboxylate) |
| SMPB | (succinimidyl 4-(p-maleimidophenyl)butyrate) |
| SPDP | (succinimidyl 3-(2-pyridyldithio)proprionate) |
| Sulfo-GMBS | (N-γ(maleimidobutyryloxy)sulfosuccinimide ester) |
| Sulfo-EMCS | (N-ε(maleimidocaproyloxy)sulfosuccinimide ester). |

Examples of linker molecules for connecting SH and SH functions are:

| BMB | (1.4-bis-maleimidobutane) |
| BMDB | (1.4-bis-maleimido-2,3-dihydroxybutane) |
| BMH | (bis-maleimidohexane) |
| BMOE | (bis-maleimidoethane) |
| DTME | (dithio-bis-maleimidoethane) |
| HBVS | (1.6-hexane-bis-vinyl sulfone) |
| BM(PEO)$_3$ | (1.8-bis-maleimidotriethylene glycol) |
| BM(PEO)$_4$ | (1.11-bis-maleimidotetraethylene glycol). |

Examples of linker molecules for connecting NH and NH functions are:

| BSOCOES | (bis-(2-succinimidyloxycarbonyloxy)ethyl) sulfone |
| BS$^3$ | (bis-(sulfosuccinimidyl) suberate) |
| DFDNB | (1.5-difluoro-2,4-nitrobenzene) |
| DMA | (dimethyl adipimidate HCl)) |
| DSG | (disuccinimidyl glutarate) |
| DSS | (disuccinimidyl suberate) |
| EGS | (ethylene glycol bis(succinimidyl succinate). |

Examples of linker molecules for connecting SH and CHO functions are:

| BMPH | (N-(β-maleimidopropionic acid)hydrazide TFA) |
| EMCA | (N-(ε-maleimidocaproic acid)hydrazide) |
| KMUH | (N-(κ-maleimidoundecanoic acid)hydrazide) |
| M$_2$C$_2$H | (4-(N-maleimidomethyl)cyclohexane-1-carboxyl-hydrazide HCl) |
| MPBH | (4-(4-N-maleimidophenyl)butyric acid hydrazide HCl) |
| PDPH | (3-(2-pyridyldithio)propionylhydrazide). |

An example of a linker molecule for connecting SH and OH functions is

| PMPI | (N-(p-maleimidophenyl) isocyanate). |

Examples of linker molecules for converting an SH function into a COOH function are

| BMPA | (N-β-maleimidopropionic acid) |
| EMCH | (N-β-maleimidocaproic acid) |
| KMUA | (N-κ-maleimidoundecanoic acid). |

Examples of linker molecules for converting an NH function into a COOH function are MSA (methyl N-succinimidyl adipate) or longer-chain homologues thereof or corresponding derivatives of ethylene glycol.

Examples of linker molecules for converting a COOH function into an NH function are DAB (1.4-diaminobutane) or longer-chain homologues thereof or corresponding derivatives of ethylene glycol.

An example of a linker molecule which reacts with an amino group of a molecule and provides a protected amino group at a larger distance from this molecule to avoid steric hindrance is TFCS(N-ε(trifluoro-acetylcaproyloxy) succinimide ester).

Further suitable linker molecules are known to skilled workers and commercially available or can be designed as required and depending on the functional groups present and desired in the HAS and the lower molecular weight substances to be coupled on, and be prepared by known methods.

In a particularly preferred preparation method, the terminal aldehyde group of HAS is selectively oxidized with a molar excess of iodine, preferably in a molar ratio of iodine to HAS of from 2:1 to 20:1, particularly preferably about 5:1 to 6:1, in aqueous basic solution. In the optimized method described in example 1, initially an amount of hydroxyalkylstarch is dissolved in hot distilled water, and somewhat less than 1 mole equivalent of aqueous iodine solution, preferably in a concentration of about 0.05-0.5N, particularly preferably about 0.1N, is added. After this, an aqueous NaOH solution in a molar concentration which is about 5-15 times, preferably about 10 times, that of the iodine solution is slowly added dropwise, at intervals of several minutes, to the reaction solution until the solution starts to become clear again after the addition. Somewhat less than 1 mole equivalent of the above aqueous iodine solution is again added to the reaction solution, the dropwise addition of the NaOH solution is resumed, and the addition of iodine and NaOH are repeated until an approximately 5.5-6 mole-equivalent iodine solution and an 11-12 mole-equivalent NaOH solution, based on the hydroxyalkylstarch, have been added. The reaction is then stopped, the reaction solution is desalted, e.g. by dialysis or ultrafiltration, subjected to a cation exchange chromatography, and the reaction product is obtained by lyophilization. In this method, virtually quantitative yields are achieved irrespective of the molecular weight of the HAS.

In a further particularly preferred embodiment, the selective oxidation takes place with alkaline stabilized solutions of metal ions, e.g. $Cu^{++}$ or $Ag^+$, likewise in approximately quantitative yields (Example 2). It is preferred in this case to employ an approximately 3-10 times molar excess of the oxidizing agent.

The selectively oxidized hydroxyalkylstarch which has formed is subsequently reacted in a suitable organic solvent with a primary amino group of the desired low molecular weight substance to form an amide linkage. Preferred solvents have been selected from the group of polar nonprotic solvents, and dimethyl sulfoxide (DMSO) has been particularly preferably used. In contrast to conventional methods described in the literature for similar coupling reactions, in this case it has surprisingly been found that the use of otherwise obligatory activators such as carbodiimides and triazoles is unnecessary. The coupling of selectively oxidized hydroxyethylstarch (ox-HES) to various model compounds (see examples) proceeded smoothly even in the absence of an activator.

However, the coupling reactions preferably take place in the presence of a carbodiimide, more preferably in the presence of DCC (dicyclohexyldicarbodiimide), most preferably in the presence of EDC (1-(3-dimethylaminopropyl)-3-ethylcarbodiimide).

The reactive group of the hydroxyalkylstarch molecule can also be an amine or thiol group produced by chemical reaction of the terminal aldehyde group. For example, a reductive amination of the aldehyde group can be carried out by reaction with ammonia in the presence of hydrogen and a catalyst or in the presence of sodium cyanoborohydride. The resulting amine or thiol group can then react with a free carboxyl group or aldehyde group of the low molecular weight substance. The initial results in this case are amide or thioester linkages or Schiff's bases, which can be modified where appropriate by a further reaction.

A further possibility is for the terminal aldehyde group of the hydroxyalkylstarch molecule or a functional group derived therefrom by chemical reaction also to be reacted with a suitable physiologically tolerated bifunctional linker molecule. In this case, the "functional group derived from the terminal aldehyde group of the hydroxyalkylstarch molecule by chemical reaction" for the coupling reaction is the remaining reactive functional group of the bifunctional linker molecule with which the terminal aldehyde group or the functional group derived therefrom has been reacted. It is possible in this way likewise to convert the terminal aldehyde group into a desired functional group.

Suitable linker molecules comprise at one end a group able to enter into a covalent bonding with the terminal aldehyde group or a functional group derived therefrom by chemical reaction, e.g. a carboxyl group, activated carboxyl group, amino or thiol group, and at the other end a group being able to enter into a covalent bonding with a reactive functional group of the low molecular weight substance, e.g. an amino, thiol, carboxyl or OH group, preferably aryl-OH group. Between the two functional groups of the linker molecule there is a biocompatible bridging molecule of suitable length, e.g. a grouping derived from an alkane, an (oligo)alkylene glycol grouping or another suitable oligomer grouping. Preferred groupings able to react with amino groups are, for example, N-hydroxysuccinimide esters, sulfo-N-hydroxysuccinimide esters, imido esters or other activated carboxyl groups; preferred groupings able to react with thiol groups are, for example, maleimide and carboxyl groups; preferred groupings able to react with aldehyde or carboxyl groups are, for example, amino or thiol groups.

A number of specific, non-restrictive examples of suitable linker molecules have already been indicated above with reference to the conjugation of linker molecules to low molecular weight substances.

In an alternative inventive coupling method of the present invention, the terminal aldehyde group of the hydroxyalkylstarch (HAS) is reacted directly with a primary amino group of the low molecular weight substance or of a linker molecule coupled to this substance, to form a Schiff's base. The formed Schiff's base is, subsequent or parallel thereto, reduced to the amine by reaction with a suitable reducing agent, resulting in a bonding which is stable in aqueous medium between low molecular weight substance and HAS.

Preferred reducing agents are sodium borohydride, sodium cyanoborohydride, organic boron complexes, e.g. a 4-(dimethylamino)pyridine-boron complex, N-ethyldiisopropylamine-boron complex, N-ethylmorpholine-boron complex, N-methylmorpholine-boron complex, N-phenylmorpholine-boron complex, lutidine-boron complex, triethylamine-boron complex, trimethylamine-boron complex; suitable stereoselective reducing agents are, for example, sodium triacetate borohydride, sodium triethylborohydride, sodium trimethoxyborohydride, potassium tri-sec-butylborohydride (K-Selectride), sodium tri-sec-butylborohydride (N-Selectride), lithium tri-sec-butylborohydride (L-Selectride), potassium triamylborohydride (KS-Selectride) and lithium triamylborohydride (LS-selectride).

The coupling reaction of HAS or oxidized HAS to a low molecular weight substance is, because the solubility in water of the substance is expected to be poor and the stability of the lactone in aqueous medium is low, preferably carried out in an organic solvent, more preferably in a polar, nonprotic solvent in which the HAS and preferably also the low molecular weight substance is soluble. Examples of suitable solvents for HAS are DMSO, glycol, diglycol, triglycol and N-methylpyrrolidone. It is also possible to employ mixtures of DMSO with other solvents if the low molecular weight substance is insoluble in DMSO or another preferred solvent for HAS. The reaction can, however, also sometimes be carried out advantageously in heterogeneous phase.

The molar ratio of HAS to low molecular weight substance in the coupling reaction is usually about 20:1 to 1:1, preferably about 5:1 to 1:1.

The coupling yields based on the low molecular weight substance are usually more than 40%, frequently more than 60% and not uncommonly more than 80% (cf. examples).

The low molecular weight substance to be coupled is preferably an active pharmaceutical ingredient whose solubility in aqueous medium and/or whose bioavailability, stability and residence time in the body are to be increased. The term "low molecular weight substance" is intended also to include peptides of up to about 50 amino acids. The active pharmaceutical ingredient is preferably selected from the group composed of antibiotics, antidepressants, antidiabetics, antidiuretics, anticholinergics, antiarrhythmics, antiemetics, antitussives, antiepileptics, antihistamines, antimycotics, antisympathotonics, antithrombotics, androgens, antiandrogens, estrogens, antiestrogens, antiosteoporotics, antitumor agents, vasodilators, other antihypertensive agents, antipyretic agents, analgesics, antiinflammatory agents, β-blockers, immunosuppressants and vitamins.

Some non-restrictive examples of active pharmaceutical ingredients having an $NH_2$ group as partner in the coupling reaction with HAS are:

albuterol, alendronate, amikazin, ampicillin, amoxicillin, amphotericin B, atenolol, azathioprine, cefaclor, cefadroxil, cefotaxime, ceftazidime, ceftriaxone, cilastatin, cimetidine, ciprofloxacin, clonidine, colistin, cosyntropin, cycloserine, daunorubicin, doxorubicin, desmopressin, dihydroergotamine, dobutamine, dopamine, ephedrine, epinephrine, ε-aminocaproic acid, ergometrine, esmolol, famotidine, flecainide, folic acid, flucytosine, furosemide, ganciclovir, gentamicin, glucagon, hydrazaline, imipenem, isoproterenol, ketamine, liothyronine, LHRH, merpatricin, metaraminol, methyldopa, metoclopramide, metoprolol, mexiletine, mitomycin, neomicin, netilmicin, nimodipine, nystatin, octreotide, oxytocin, pamidronate, pentamidine, phentolamine, phenylephrine, procainamide, procaine, propranolol, ritodrine, sotalol, teicoplanin, terbutaline, thiamine, tiludronate, tolazoline, trimethoprim, tromethamine, vancomycin, vasopressin and vinblastine.

Preferred examples of active pharmaceutical ingredients having an $NH_2$ group as partner in the coupling reaction with HAS are 6-aminopenicillic acid, 7-aminocephalosporin, 7-aminocephalosporanic acid and 7-aminopenicillanic acid.

Specific examples of those active ingredients having a COOH group as partner for the coupling reaction with HAS are:

acetylcysteine, azlocillin, aztreonam, benzyl-penicillin, camptothecin, cefamandole, cefazolin, cefepime, cefotaxime, cefotetan, cefoxitin, ceftazidime, ceftriaxone, cephalothin, cilastatin, ciprofloxacin, clavulanic acid, dicloxacillin, ε-aminocaproic acid, floxacillin, folinic acid, furosemide, fusidic acid, imipemem, indomethacin, ketorolac, liothyronine, melphalan, methyldopa, piperacillin, prostacyclin, prostaglandins, teicoplanin, ticarcillin and vancomycin.

Specific examples of those active ingredients having an aryl-OH group as partner in the coupling reaction with HAS are:

albuterol, allopurinol, apomorphine, ceftriaxone, dobutamine, dopamine, doxycycline, edrophonium, isoproterenol, liothyronine, metaraminol, methyldopa, minocycline, pentazocine, phenylephrine, phentolamine, propofol, rifamycins, ritodrine, teicoplanin, terbutaline, tetracycline and vancomycin.

Specific examples of those active ingredients having an aliphatic OH group as partner in the coupling reaction with HAS are are Taxol and palcitaxel.

The reaction products of the chemical coupling described above can be investigated by known methods, and the coupling efficiency can be established. For example, a UV calibration plot for the relevant low molecular substance can be constructed and used to determine the content of low molecular weight substance in the sample or the proportion of low molecular weight substance in the coupling product. If the low molecular weight substance shows no UV absorption, appropriate colorimetry or electrochemical detection methods can be developed in analogy to known methods. The saccharide content in the conjugate can be detected for example by a glycan-specific staining of the fractionated reaction products. Quantitative glycan determination is also possible. The coupling yield of reactions involving primary amines could also be established by derivatization of the unreacted amines with fluorescamine and determination of the fluorescence.

The improved solubility in water can easily be checked in the case of slightly soluble starting materials by dissolution tests. In the case of coupling with partially water-soluble active pharmaceutical ingredients, the increased hydrophilicity can be determined by means of an OECD method to measure the logP value. This correlates the retention time of substances in RP-HPLC with the partition coefficient in an n-octanol/water mixture. All HES conjugates of the invention investigated by this method eluted in the hold-up volume of a C18 column, and thus showed no interactions with the C18 material.

The conjugates of the present invention can where appropriate be employed as such or in the form of a pharmaceutical composition for the prophylactic or therapeutic treatment of the human or animal body.

Compositions of this type include a pharmaceutically effective amount of a conjugate of the invention as active ingredient, and a pharmaceutically suitable carrier and, where appropriate, other therapeutic or pharmaceutical ingredients or excipients. Excipients may include for example diluents, buffers, flavorings, binders, surface-active agents, thickeners, lubricants, preservatives (including antioxidants) and substances which serve to make the formulation isotonic with the blood of the intended recipient. A pharmaceutically effective amount is the amount sufficient to display on single or multiple administration a desired beneficial effect during a treatment to alleviate or cure or prevent a pathological condition. A pharmaceutically acceptable carrier is a carrier which is compatible both with the active pharmaceutical ingredient and with the patient's body.

The form of the composition will vary depending on the desired or suitable administration route. Suitable administration routes may be for example oral, parenteral, e.g. subcutaneous, intramuscular, intra-venous, intraarterial, intraarticular, intrathecal, extradural injection or, where appropriate, infusion, intranasal, intratracheal, rectal or topical administration. The pharmaceutical compositions may beneficially be supplied in the form of a dosage unit and be produced by any method well known in the pharmacy sector.

The HAS conjugates of the present invention can also be employed in all other sectors in which other polymer conjugates, e.g. PEG conjugates, have been used. Some specific, non-restrictive examples are the use of an HAS conjugate as immobilized reactant for a reaction in heterogeneous phase or as column material for affinity chromatography. Further possible uses will be plainly evident to the skilled worker with knowledge of the properties disclosed herein of the HAS conjugates of the invention.

The following examples are intended to explain the invention in more detail without, however, restricting it thereto. In particular, analogous reactions can also be carried out with hydroxymethylstarch and hydroxypropylstarch, and similar results can be achieved.

EXAMPLE 1

Selective Oxidation of Hydroxyethylstarch (HES) with Iodine 10 g of HES-130 kD were dissolved in 12 ml of deionized water by heating in a round-bottomed flask. 2 ml of an 12 solution (0.1N) were added to this solution. A pipette with 2 ml of 1.0N NaOH was connected to the flask via a 2-way connector, and the NaOH solution was added dropwise at about 1 drop every 4 minutes. The solution was decolorized after addition of approximately 0.2 ml of the NaOH solution and, at this time, a second portion of 2 ml of 0.1N iodine solution was added. The reaction was complete after addition of a total of 14 ml of iodine solution and 2.8 ml of NaOH solution. The reaction mixture was then dialyzed against deionized water.

Lactonization:

The partially desalted solution was subjected to a chromatography on a cation exchange column (Amberlite IR-120, H$^+$ form) in order to convert the aldonate groups into aldonic acid groups. Subsequently, the water was removed by lyophilization, and thus the lactone form was obtained.

Determination of the Degree of Oxidation:

1 ml of alkaline copper reagent (3.5 g of $Na_2PO_4$, 4.0 g of K Na tatrate in 50 ml of $H_2O$, plus 10 ml of 1N NaOH, 8.0 ml of 10% strength (weight/volume) $CuSO_4$ solution and 0.089 g of K iodate in 10 ml of $H_2O$, after addition of 18 g of Na sulfate, make up to 100 ml) are pipetted into 1 ml of sample solution in each case under an $N_2$ atmosphere. The mixture is heated at 100° C. for 45 minutes. After cooling, 0.2 ml of 2.5% strength KI solution and 0.15 ml of 2M $H_2SO_4$ are added. After 5 min, 1 drop of phenol red indicator solution (1% weight/volume) is added, and titration is carried out with 5 mM $Na_2S_2O_3$ solution until the color disappears. The concentration of unreacted aldehyde groups can be calculated from the consumption of titrant.

An approximately quantitative yield was achieved (>98%). It is possible by this procedure to oxidize hydroxyethylstarches with higher molecular weight (e.g. 130 kD, 250 kD, 400 kD) just like hydroxyethylstarches with lower molecular weight (e.g. 10 kD, 25 kD, 40 kD), in similarly high yields.

EXAMPLE 2

Selective Oxidation of HES with $Cu^{2+}$ Ions

A solution of 0.24 mmol of HES-130 kD was prepared in 10 ml of deionized water with heating. This solution was heated in a 100 ml round-bottomed flask to a temperature of 70-80° C., and 1.17 mmol of stabilized $Cu^{2+}$ (e.g. Rochelle salt as stabilizer or other stabilizers) and dilute aqueous NaOH solution was added (final concentration 0.1N NaOH). The temperature was then raised to 100° C., and the reaction was allowed to proceed until a reddish color had appeared. The reaction was stopped and the reaction mixture was cooled to 4° C. The reddish precipitate was removed by filtration. The filtrate was dialyzed against deionized water and then converted into the lactone as in Example 1. The oxidation took place quantitatively (yield >99%). It was also possible by this method to oxidize low molecular weight HES (e.g. HES-10 kD, HES-25 kD, HES-40 kD) and higher molecular weight HES species (e.g. 130 kD, 250 kD, 400 kD).

EXAMPLE 3

Coupling of Selectively Oxidized Hydroxyethylstarch (ox-HES) to Alendronate 5 mg of alendronate (a bisphosphonate) and a 3-5-fold molar excess of ox-HES lactone (prepared as described in Example 1 or 2) were dissolved in 4-5 ml of DMSO in a 100 ml round-bottomed flask. The suspension was heated to 70° C. and left for 24-36 hours with moderate stirring (magnetic stirrer). The reaction was then stopped and the reaction mixture was cooled to room temperature. Then 20-30 ml of water were added, and this solution was dialyzed against distilled water. Instead of dialysis it is also possible to employ an ultrafiltration with a suitable exclusion limit of the membrane. This makes it possible not only to exchange the solvent but also to concentrate the solution, which is subsequently lyophilized. The success of the coupling is demonstrated by means of standard analytical methods, e.g. gel permeation chromatography and ninhydrin test for free amino groups. The yield of coupling product was about 85% for the coupling with ox-HES-130 kD and about 80% for coupling with ox-HES-10 kD lactone.

EXAMPLE 4

Coupling of Selectively Oxidized RES (ox-HES) to Amphotericin B 12.0 g of dried ox-HES-130 kD lactone were dissolved in 30 ml of dry DMSO in an $N_2$ atmosphere. The solution was heated to 70° C., and 52 mg of amphotericin B were added. The reaction was left with exclusion of light under these conditions for 24 h. Successful coupling was demonstrated by gel permeation chromatography with photometric detection at 385 nm ($\lambda_{max}$ of amphotericin). After completion of the reaction, it was stopped by adding 80 ml of distilled water and intensively dialyzed against water. Lyophilization afforded a pale yellow coupling product. (Yield about 87%).

Under comparable conditions, a yield of about 75% was achieved in the coupling of ox-HES-10 kD lactone with amphotericin B.

EXAMPLE 5

Coupling of ox-HES to Ampicillin 1.3 g of dry ox-HES-130 kD lactone were dissolved in 5 ml of dry DMSO in a 100 ml round-bottomed flask. This solution was heated to 45° C., and 11.0 mg of ampicillin (Aldrich # 27.186-1) were added. The reaction took place with moderate stirring for 20 h and was stopped after this time by adding 25 ml of distilled water. The reaction mixture was dialyzed against distilled water and then lyophilized. The success of coupling was demonstrated by analyzing the product with GPC and determining the free amino groups on the ampicillin using ninhydrin.

EXAMPLE 6

Coupling of ox-HES to Neomycin $3\times10^{-5}$ mol of ox-HES-25 kD lactone were dissolved in 5 ml of N-methylpyrrolidone in a 50 ml reaction vessel at 60° C. with magnetic stirring. Addition of 10 mg of neomycin in 2 ml of dry DMSO was followed by boiling under reflux for about 10 h. After cooling to room temperature, the reaction was stopped by adding a further 35 ml of water. Most of the solvent was removed by dialysis, and the coupling product was then lyophilized. It was possible to demonstrate coupling product in a yield of about 82% by GPC with UV detection.

EXAMPLE 7

Coupling of ox-HES to Mepartricin 10 ml of ethylene glycol were needed to completely dissolve 2.5 g of ox-HES-130 kD lactone and 22 mg of mepartricin (obtainable from Societá Prodotti Antibiotici, Milan, Italy) with heating. The solvent had previously been degassed and dried. The reaction solution was stirred with exclusion of light under an inert gas atmosphere for 36 h, and the reaction was finally stopped by introducing 40 ml of ice-cold water. The ethylene glycol was removed by ultrafiltration (10 kD membrane), and subsequent lyophilization afforded 2.1 g of pale yellowish powder. Further purification took place by RP-HPLC on a C18 column with UV/VIS detection.

EXAMPLE 8

Coupling of ox-HES to Nystatin 2.5 g of dry ox-HES-130 kD lactone were dissolved in 10 ml of dry DMSO in a 100 ml round-bottomed flask. Addition of 9.5 mg of nystatin was followed by heating to 60° C. and stirring in the dark under an inert gas atmosphere. The reaction took place with moderate stirring for 48 h and was stopped after this time by adding 50 ml of distilled water. The reaction mixture was dialyzed against distilled water and then lyophilized. Successful coupling was demonstrable by RP-HLPC(C18 column) and detection at 325 nm. The yield estimated from the absorption of the product peak was about 67%.

EXAMPLE 9

Coupling of ox-HES to Mitomycin C 2.5 g of ox-HES-130 kD lactone and 20 g of mitomycin (Fluka # 69824) were dissolved in 10 ml of a 9:1 DMSO:MeOH mixture at 60° C. The reaction solution was kept under reflux for 24 h and then 40 ml of water were added to stop the reaction. This solution was dialyzed against deionized water overnight and then subjected to a freeze drying. Coupling was demonstrated by RP-HPLC and detection at 320 nm. The expected coupling product resulted in a yield of 82%.

EXAMPLE 10

Coupling of ox-HES to Daunorubicin 1.3 g of ox-HES-130 kD lactone were dissolved in 10 ml of N-methylpyrrolidone with stirring at 70° C. 17 mg of daunorubicin (Fluka #30450), dissolved in 3 ml of DMF, were added dropwise thereto. The reaction mixture was stirred under these conditions for 20 h, cooled to room temperature and finally shaken with 40 ml of distilled water. Most of the solvent was removed by dialysis against water, followed by freeze drying. The coupled daunorubicin was demonstrated by RP-HPLC and UV-VIS detection.

EXAMPLE 11

Coupling of ox-HES to 7-aminocephalosporin 3.0 g of ox-HES-130 kD lactone and 20 mg of 7-aminocephalosporin (Fluka #07300) were dissolved in 5 ml of dry DMSO in a 100 ml round-bottomed flask with magnetic stirring. The temperature was raised to 50° C. and maintained for 15 h. After this time, the reaction mixture was cooled to 25° C. and diluted by adding 5 ml of distilled water. DMSO and unreacted 7-amino-cephalosporin were removed by dialysis against distilled water. The solution was then lyophilized and the product was analyzed by TLC and GPC.

EXAMPLE 12

Coupling of ox-HES to 6-aminopenicillic Acid

The reaction described in Example 11 was also carried out with 16 mg of 6-aminopenicillic acid instead of 7-aminocephalosporin under the same conditions, and the reaction product was worked up and analyzed under the same conditions.

EXAMPLE 13

Coupling of ox-HES to LHRH 1.0 g of dried ox-HES-130 kD lactone was incubated with 5 mg of LHRH (luteinizing hormone-releasing hormone) (Bachem, Switzerland) in 10 ml of dry DMSO. The reaction proceeded while stirring at 45° C. for 15 h and was stopped by adding 40 ml of water. Hesylated LHRH was obtained by lyophilization after it had been extensively dialyzed against water in order to remove most of the DMSO and unreacted peptide. The resulting product was analyzed by GPC (Superose 12, Amersham-Pharmacia, Sweden) and UV detection at 280 nm. A stoichiometry of approximately 1:1 for the coupling product emerged from the quantification of the peptide on the basis of the Trp absorption and the quantification of the polysaccharide content by phenol/sulfuric acid coloring.

EXAMPLE 14

Coupling of ox-HES to Camptothecin 20 mg of camptothecin were dissolved in 5 ml of dry DMSO at 5° C. in a round-bottomed flask. 36 mg of 1.4-diaminobutane in 2 ml of dry DMSO were added dropwise to this solution. The reaction mixture was left to stir gently under these conditions for 24 h. The conjugation product was purified by flash chromatography. The yield was about 83%.

For the coupling reaction of the modified camptothecin with ox-HES-130 kD, the complete reaction mixture was dissolved after purification together with 3.6 g of the polysaccharide lactone in 8 ml of dry DMSO by stirring and heating at 50° C. The progress of the reaction was followed by RP-HPLC of samples from the reaction mixture. After 20 h at 50° C., no further product formation was observable, and the reaction was stopped by adding 50 ml of distilled water. After dialysis against water, the coupling product was freeze dried. Analysis took place by GPC and staining of the free amino group in the modified, unreacted camptothecin with ninhydrin on a TLC plate.

EXAMPLE 15

Coupling of ox-HES to Prostacyclin a) Amino Functionalization 352 mg of prostacyclin (Sigma-Aldrich) were dissolved in 5 ml of dry DMF with 2% methylene chloride (V/V) at 0° C. 1.3 g of dicyclohexylcarbodiimde (DCC) in 5 ml of dry DMF were added thereto. Reaction was allowed to take place while stirring gently for 30 minutes. Then a 5-fold molar excess (based on prostacyclin) of 1.5-diaminoethyl ether was added, and the solution was slowly warmed to room temperature. The amino-functionalized coupling product was purified by flash chromatography on a silica phase.

b) Hesylation 220 mg of the purified coupling product from a) were dissolved in 8 ml of glycol at room temperature. 4.0 g of ox-HES-130 kD lactone, dissolved in 10 ml of glycol, were admixed with stirring and heated to 45° C. After a reaction time of 8 h, the mixture was cooled in an ice bath and dialyzed intensively against water. The clear solution was investigated by RP-HPLC on a C18 column. It was possible to calculate the coupling efficiency from the ratio of the areas in the hold-up volume of the column (coupling product) and the initial substance. The yield was 53%.

EXAMPLE 16

Coupling of HES to Alendronate

A ten-fold molar excess of HES-25 kD was added to a solution of 2.25 mg of alendronate in 4 ml of phosphate buffer (0.1M, pH 7.5) in a 100 ml round-bottomed flask. The reaction mixture was shaken in order to dissolve the polysaccharide completely, and then a thirty-fold molar excess of $NaBH_3CN$ was added. The reaction proceeded at room temperature for 48 h, the production of a coupling product being detected in an aliquot by reaction with fluorescamine, which yields a fluorescent product with free amino groups.

EXAMPLE 17

Coupling of HES to Amoxillin 4.0 ml of 0.1N Na phosphate buffer (pH 7.5) were introduced into a two-neck flask, and 1.5 g of HES-40 kD were dissolved therein by heating to 60° C. After cooling to 25° C., 7.0 mg of amoxillin (Fluka #10039) were added with magnetic stirring. A solution of $NaBH_3CN$ corresponding to a thirty-fold molar excess was prepared in 2 ml of the same Na phosphate buffer in a separate vessel. The cyanoborohydride solution was slowly added dropwise, using a dropping funnel, to the first solution over a period of 30 minutes. The reaction mixture was stirred for a further 24-36 h and then the pH was adjusted to 4 with 0.1N HCl to stop the reaction. The solution was desalted by dialysis and lyophilized. Demonstration of the coupling product took place by GPC and UV photometer.

EXAMPLE 18

Coupling of HES to Cefaclor 4 ml of 0.1N Na phosphate buffer (pH 7.0) were used to dissolve 110 mg of $NaBH_3CN$ in a 100 ml round-bottomed flask. $6.0 \times 10^{-5}$ mol of HES-130 kD and $2.0 \times 10^{-5}$ mol of cefaclor (Fluka #22125) were added while stirring. The reaction temperature was kept at 25° C., and the reaction mixture was stirred moderately for 24 h. The solution was then acidified to pH 4.0 and stirred for a further 30 minutes. Desalting and concentration were carried out by ultrafiltration (10 kD membrane). The coupling product was demonstrated by HP-GPC at 265 nm.

EXAMPLE 19

Coupling of HES to Doxorubicin 6.0 mg of doxorubicin (Fluka #45584) were suspended in 4 ml of 0.1N Na phosphate buffer (pH 7.5) in the presence of a three-fold molar excess of HES-130 kD at room temperature. The reaction mixture was vigorously stirred for 30 minutes, and 3 ml of a 0.8M $NaBH_3CN$ solution was slowly added. The reaction was kept at room temperature with stirring for 48 h. A 10 kD membrane was then used for diafiltration in order to remove salts and unreacted doxorubicin. The diafiltered solution was lyophilized and the coupling product was investigated by GPC and RP-HPLC.

EXAMPLE 20

Coupling of HES to Vasopressin 1.25 g of HES-130 kD were dissolved in 5 ml of 0.1M Na phosphate buffer, pH 8.0, with heating and gentle stirring in a round-bottomed flask equipped with a dropping funnel. 5 mg of vasopressin (Bachem, Switzerland) were added this solution. 30 mg of $NaBH_3CN$ were dissolved in 2 ml of 0.1M phosphate buffer (pH 7.5) and slowly added dropwise through the dropping funnel to the reaction mixture. The reaction was left to stand at 25° C. for about 24 h. To terminate the reaction, the pH was lowered to 4.0 by adding 0.1N HCl. After extensive dialysis against water, the hesylated product was freeze dried. Analysis took place by GPC as described above and UV detection at 220 nm.

EXAMPLE 21

Coupling of ox-HES 70 kD to Neomycin 1.01 mg of neomycin (sulfate salt) and 126.21 mg of oxHES 70 kD were dissolved in 2 ml of DMSO in a two-neck flask under an argon atmosphere and, after addition of 0.81 mg of DMAP, heated at 70° C. for 24 h. The reaction was then stopped by adding acetone, whereupon the coupling product precipitated. The solid was dissolved in water and purified by dialysis against water for 48 h. Freeze drying resulted in 80 mg of white coupling product (63%).

EXAMPLE 22

Alternative Method for Coupling of ox-HES 70 kD to Neomycin

Coupling of neomycin to ox-HES 70 kD can likewise be carried out successfully at room temperature in DMSO with addition of EDC as activator. For this purpose, 16.97 mg of neomycin (sulfate salt), 348 mg of ox-HES 70 kD and 2.28 mg of DMAP were dissolved in 1 ml of DMSO. After addition of 3.83 mg of DCC (1 equivalent), the solution was stirred for 2 h and the addition of one equivalent of DCC was repeated. This process was repeated until 10 equivalents of DCC had been added to the reaction solution. The reaction time totaled 24 h. After addition of 20 ml of acetone to the solution, the coupling product precipitated. The solid was dissolved in water and purified by dialysis against water for 48 h. Freeze drying resulted in 280 mg of white coupling product (80%).

EXAMPLE 23

Coupling of ox-HES 70 kD to Daunorubicin 0.5 mg of daunorubicin hydrochloride, 829.2 mg of ox-HES 70 kD and 0.108 mg of DMAP were dissolved in 2 ml of DMSO under an argon atmosphere in a two-neck flask and heated at 70° C. for 24 h. Then acetone (20 ml) was added thereto, whereupon the coupling product precipitated. The solution was centrifuged and the precipitate was washed with acetone and centrifuged several times. A pale pink-colored solid was obtained and was dissolved in water and dialyzed against water. Freeze drying results in 656 mg (80%) of a pale pink-colored solid. The purity of the coupled daunorubicin was checked by RP-HPLC.

EXAMPLE 24

Coupling of ox-HES 130 kD to 7-aminocephalosporanic Acid 383 mg of ox-HES-130 kD and 1.22 mg of 7-amino-cephalosporanic acid (Fluka #07300) were dissolved in 2 ml of dry DMSO in a 100 ml round-bottomed flask with magnetic stirring. The temperature was raised to 70° C. and maintained for 24 h. After this time, the mixture was cooled to 25° C., and the reaction product was precipitated by adding 20 ml of acetone. The solid was washed with 20 ml of acetone and dissolved in 20 ml of distilled water. Further purification of the coupling product took place by dialysis against distilled water. The solution was then lyophilized and the product was analyzed by TLC and GPC. 270 mg of coupling product (70%) were obtained in the form of a white solid.

EXAMPLE 25

Coupling of ox-HES 70 kD to 6-aminopenicillanic Acid

The reaction described in Example d was also carried out with 1.57 mg of 6-aminopenicillanic acid instead of 7-aminocephalosporanic acid and 135.54 mg of ox-HES 70 kD under the same conditions. The reaction product was worked up and analyzed under the same conditions. After purification, 88 mg of coupling product (65%) were obtained as white solid.

EXAMPLE 26

Coupling of HES 40 kD to Amoxicillin 4.0 ml of 0.1N Na phosphate buffer (pH 7.5) were introduced into a two-neck flask, and 1.5 of HES-40 kD were dissolved therein by heating to 60° C. After cooling to 25° C., 7.0 mg of amoxicillin (Fluka #10039) were added with magnetic stirring. A solution of $NaBH_3CN$ corresponding to a thirty-fold molar excess was prepared in 2 ml of the same Na phosphate buffer in a separate vessel. The cyanoborohydride solution was slowly added dropwise with the aid of a dropping funnel to the first solution over a period of 30 minutes. The reaction mixture was stirred for a further 24-36 h, and then the pH was adjusted to 4 with 0.1N HCl to stop the reaction. The solution was desalted by dialysis and lyophilized. Demonstration of the coupling product took place by GPC and UV photometer.

EXAMPLE 27

Coupling of ox-HES 70 kD to Amoxicillin 173 mg of ox-HES 70 kD and 0.85 g of amoxicillin were dissolved in 2 ml of dry DMSO in a 100 ml round-bottomed flask with magnetic stirring. The temperature was raised to 70° C. and maintained for 24 h. After this time, the mixture was cooled to 25° C., and the reaction product was precipitated by adding 20 ml of actone. The solid was washed with 20 ml of acetone and dissolved in 20 ml of distilled water. Further purification of the coupling product took place by dialysis against distilled water. The solution was then lyophilized, and the product was analyzed by TLC and GPC. 151 mg of coupling product (87%) are obtained in the form of a white solid.

EXAMPLE 28

Coupling of ox-HES 70 kD to Cefadroxil 610 mg of ox-HES 70 kD and 2.965 mg of cefadroxil were dissolved in 2 ml of dry DMSO in a 100 ml round-bottomed flask with magnetic stirring. The temperature was raised to 70° C. and maintained for 24 h. After this time, the mixture was cooled to 25° C., and the reaction product was precipitated by adding 20 ml of actone. The solid was washed with 20 ml of acetone and dissolved in 20 ml of distilled water. Further purification of the coupling product took place by dialysis against distilled water. The solution was then lyophilized, and the product was analyzed by TLC and GPC. 490 mg of coupling product (87%) are obtained in the form of a white solid.

EXAMPLE 29

Coupling of ox-HES 70 kD to Glucagon

Glucagon ($66 \times 10^{-9}$ mol, 0.23 mg), oxHES 70 kD ($6.6 \times 10^{-6}$ mol, 123 mg) are dissolved in 1 ml of DMSO in a round-bottomed flask. At intervals of 1 h, DDC is added in 8 portions at 1 h intervals until a total of 23.08 mg have been added to the reaction solution. After a reaction time of 24 h, the reaction is stopped by adding 15 ml of water. The coupling product purified by dialysis against water. Freeze drying results in 79 mg of white coupling product (65%).

The invention claimed is:

1. A conjugate of hydroxyalkylstarch (HAS) and a low molecular weight substance, obtained by a process that comprises selectively coupling (i) the terminal aldehyde group of a HAS molecule, or a functional group derived from this aldehyde group, wherein the functional group derived from the aldehyde group is one of the functional groups of a bifunctional linker molecule with which the terminal aldehyde group has been reacted, with (ii) a functional group on the low molecular weight substance, which is able to react with the terminal aldehyde group of the HAS molecule or the functional group derived therefrom, wherein the coupling reaction results in a covalent bond between the terminal aldehyde of the HAS molecule or the functional group derived therefrom and the low molecular weight substance functional group, or wherein the coupling reaction is modified by a further reaction to give the abovementioned covalent bond, wherein the low molecular weight substance is an active pharmaceutical ingredient, (a) wherein the functional group of the active pharmaceutical ingredient involved in the coupling reaction is an amino group and the active pharmaceutical ingredient is selected from the group consisting of albuterol, alendronate, amikazin, aminopenicillin, amoxicillin, atenolol, azathioprine, cefaclor, cefadroxil, cefotaxime, ceftazidime, ceftriaxone, cilastatin, cimetidine, ciprofloxacin, clonidine, colistin, cosyntropin, cycloserine, daunorubicin, doxorubicin, desmopressin, dihydroergotamine, dobutamine, dopamine, ephedrine, epinephrine, ε-aminocaproic acid, ergometrine, esmolol, famotidine, flecainide, folic acid, flucytosine, furosemide, ganciclovir, gentamicin, glucagon, hydrazaline, imipenem, isoproterenol, ketamine, liothyronine, LHRH, merpatricin, metaraminol, methyldopa, metoclopramide, metoprolol, mexiletine, mitomycin, neomycin, netilmicin, nimodipine, nystatin, octreotide, oxytocin, pamidronate, pentamidine, phentolamine, phenylephrine, procainamide, procaine, propranolol, ritodrine, sotalol, teicoplanin, terbutaline, thiamine, tiludronate, tolazoline, trimethoprim, tromethamine, vancomycin, vasopressin, and vinblastine, or (b) wherein the functional group of the active pharmaceutical ingredient involved in the coupling reaction is a carboxyl group or activated carboxyl group and the active pharmaceutical ingredient is selected from the group consisting of acetylcysteine, azlocillin, aztreonam, benzylpenicillin, camptothecin, cefamandole, cefazolin, cefepime, cefotaxime, cefotetan, cefoxitin, ceftazidime, ceftriaxone, cephalothin, cilastatin, ciprofloxacin, clavulanic acid, dicloxacillin, epsilonaminocaproic acid, floxacillin, folinic acid, furosemide, fusidic acid, imipemem, indomethacin, ketorolac, liothyronine, melphalan, methyldopa, piperacillin, prostacyclin, prostaglandins, teicoplanin, ticarcillin, and vancomycin, or (c) wherein the functional group of the active pharmaceutical ingredient involved in the coupling reaction is an aliphatic or aryl-OH group and the active pharmaceutical ingredient is selected from the group consisting of albuterol, allopurinol, apomorphine, ceftriaxone, dobutamine, dopamine, doxycycline, edrophonium, isoproterenol, liothyronine, metaraminol, methyldopa, minocycline, paclitaxel, pentazocine, phenylephrine, phentolamine, propofol, rifamycins, ritodrine, taxol, teicoplanin, terbutaline, tetracycline, and vancomycin.

2. The conjugate as claimed in claim 1, wherein the functional group of the low molecular weight substance is one of the functional groups of a bifunctional linker molecule which has been coupled to the low molecular weight substance.

3. The conjugate as claimed in claim 1, wherein the covalent bonding is an amine linkage which is the result of a coupling reaction between the terminal aldehyde group of the HAS molecule and a primary amino group of the low molecular weight substance to form a Schiff's base, and reduction of the Schiff's base to the amine.

4. The conjugate as claimed in claim 1, wherein the HAS molecule has a molecular weight in the range from about 70 to about 1000 kD.

5. The conjugate as claimed in claim 4, wherein the HAS molecule has a molecular weight of about 130 kD.

6. The conjugate as claimed in claim 1, wherein the HAS molecule has a degree of substitution of from about 0.3 to about 0.7.

7. The conjugate as claimed in claim 1, wherein the HAS molecule has a ratio of $C_2$ to $C_6$ substitution of from 8 to 12.

8. The conjugate as claimed in claim 1, wherein the HAS molecule is a hydroxyethylstarch molecule.

9. A pharmaceutical composition comprising an effective amount of a conjugate as claimed in claim 1 and a pharmaceutically acceptable carrier.

10. A conjugate of HAS and a low molecular weight substance, wherein the conjugate comprises at least one covalent bond between:

(i) the terminal aldehyde group of the HAS molecule, or a functional group derived from the terminal aldehyde group, wherein the functional group derived from the aldehyde group is one of the functional groups of a bifunctional linker molecule with which the terminal aldehyde group has been reacted, and (ii) a functional group of the low molecular weight substance, wherein the low molecular weight substance is an active pharmaceutical ingredient, (a) wherein the functional group of the active pharmaceutical ingredient involved in the coupling reaction is an amino group and the active pharmaceutical ingredient is selected from the group consisting of albuterol, alendronate, amikazin, aminopenicillin, amoxicillin, atenolol, azathioprine, cefaclor, cefadroxil, cefotaxime, ceftazidime, ceftriaxone, cilastatin, cimetidine, ciprofloxacin, clonidine, colistin, cosyntropin, cycloserine, daunorubicin, doxorubicin, desmopressin, dihydroergotamine, dobutamine, dopamine, ephedrine, epinephrine, ϵ-aminocaproic acid, ergometrine, esmolol, famotidine, flecainide, folic acid, flucytosine, furosemide, ganciclovir, gentamicin, glucagon, hydrazaline, imipenem, isoproterenol, ketamine, liothyronine, LHRH, merpatricin, metaraminol, methyldopa, metoclopramide, metoprolol, mexiletine, mitomycin, neomycin, netilmicin, nimodipine, nystatin, octreotide, oxytocin, pamidronate, pentamidine, phentolamine, phenylephrine, procainamide, procaine, propranolol, ritodrine, sotalol, teicoplanin, terbutaline, thiamine, tiludronate, tolazoline, trimethoprim, tromethamine, vancomycin, vasopressin, and vinblastine, or (b) wherein the functional group of the active pharmaceutical ingredient involved in the coupling reaction is a carboxyl group or activated carboxyl group and the active pharmaceutical ingredient is selected from the group consisting of acetylcysteine, azlocillin, aztreonam, benzylpenicillin, camptothecin, cefamandole, cefazolin, cefepime, cefotaxime, cefotetan, cefoxitin, ceftazidime, ceftriaxone, cephalothin, cilastatin, ciprofloxacin, clavulanic acid, dicloxacillin, epsilonaminocaproic acid, floxacillin, folinic acid, furosemide, fusidic acid, imipemem, indomethacin, ketorolac, liothyronine, melphalan, methyldopa, piperacillin, prostacyclin, prostaglandins, teicoplanin, ticarcillin, and vancomycin, or (c) wherein the functional group of the active pharmaceutical ingredient involved in the coupling reaction is an aliphatic or aryl-OH group and the active pharmaceutical ingredient is selected from the group consisting of albuterol, allopurinol, apomorphine, ceftriaxone, dobutamine, dopamine, doxycycline, edrophonium, isoproterenol, liothyronine, metaraminol, methyldopa, minocycline, palcitaxel, pentazocine, phenylephrine, phentolamine, propofol, rifamycins, ritodrine, taxol, teicoplanin, terbutaline, tetracycline, and vancomycin.

11. The conjugate of claim 10, wherein the functional group derived from the terminal aldehyde group of the HAS molecule is a functional group of a bifunctional linker coupled to the terminal aldehyde group or functional group derived therefrom.

12. The conjugate of claim 10, wherein the functional group of the low molecular weight substance is a functional group of a bifunctional linker coupled to the low molecular weight substance.

13. The conjugate of claim 10, wherein the HAS molecule has a degree of substitution of from about 0.3 to about 0.7.

14. The conjugate of claim 10, wherein the HAS molecule is a hydroxyethylstarch molecule.

* * * * *